US009527892B2

(12) United States Patent
McNeely et al.

(10) Patent No.: US 9,527,892 B2
(45) Date of Patent: Dec. 27, 2016

(54) **PROTECTIVE VACCINE BASED ON *STAPHYLOCOCCUS AUREUS* SA2451 PROTEIN**

(71) Applicant: Merck Sharp & Dohme Corp., Rahway, NJ (US)

(72) Inventors: Tessie McNeely, Gwynedd Valley, PA (US); Donna Lorraine Montgomery, Chalfont, PA (US); Leslie Cope, Hatfield, PA (US); Amita Joshi, Lansdale, PA (US); Gregory P. Pancari, Doylestown, PA (US); Hongxia Fan, North Wales, PA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 14/354,948

(22) PCT Filed: Oct. 26, 2012

(86) PCT No.: PCT/US2012/062019
§ 371 (c)(1),
(2) Date: Apr. 29, 2014

(87) PCT Pub. No.: WO2013/066731
PCT Pub. Date: May 10, 2013

(65) Prior Publication Data
US 2014/0294888 A1    Oct. 2, 2014

Related U.S. Application Data

(60) Provisional application No. 61/553,589, filed on Oct. 31, 2011.

(51) Int. Cl.
| | |
|---|---|
| *A61K 39/00* | (2006.01) |
| *A61K 39/38* | (2006.01) |
| *A61K 39/02* | (2006.01) |
| *A61K 39/085* | (2006.01) |
| *A61K 45/00* | (2006.01) |
| *A61K 47/00* | (2006.01) |
| *A01N 63/00* | (2006.01) |
| *C07K 14/31* | (2006.01) |
| *A61K 38/00* | (2006.01) |
| *A61K 39/39* | (2006.01) |
| *A61K 8/99* | (2006.01) |

(52) U.S. Cl.
CPC ............ *C07K 14/31* (2013.01); *A61K 39/085* (2013.01); *A61K 8/99* (2013.01); *A61K 38/00* (2013.01); *A61K 39/00* (2013.01); *A61K 39/39* (2013.01); *A61K 2039/505* (2013.01)

(58) Field of Classification Search
CPC ...... A61K 38/00; A61K 39/00; A61K 39/085; A61K 39/39; A61K 8/99
See application file for complete search history.

(56) References Cited

U.S. PATENT DOCUMENTS

| | | |
|---|---|---|
| 6,593,114 B1 | 7/2003 | Kunsch et al. |
| 7,410,647 B2 | 8/2008 | Foster et al. |
| 7,608,276 B2 | 10/2009 | Masignani et al. |
| 2002/0103338 A1 | 8/2002 | Choi |
| 2002/0146790 A1 | 10/2002 | Wallis |
| 2005/0053995 A1 | 3/2005 | Simpson et al. |
| 2006/0177462 A1 | 8/2006 | Anderson et al. |
| 2008/0085289 A1 | 4/2008 | Castado et al. |

FOREIGN PATENT DOCUMENTS

| | | |
|---|---|---|
| EP | 1987836 | 11/2008 |
| WO | WO 98/42868 | * 10/1998 |
| WO | WO0116292 | 3/2001 |
| WO | WO0198499 | 12/2001 |
| WO | WO02059148 | 8/2002 |
| WO | WO02094868 | 11/2002 |
| WO | WO03011899 | 2/2003 |
| WO | WO2005009378 | 2/2005 |
| WO | WO2005009379 | 2/2005 |
| WO | WO2005079315 | 9/2005 |
| WO | WO2005086663 | 9/2005 |
| WO | WO2005115113 | 12/2005 |
| WO | WO2006033918 | 3/2006 |

(Continued)

OTHER PUBLICATIONS

The CDC, Methicillin-Resistant *Staphylococcus aureus* MRSA infections, 2010, pp. 1-44.*
Archer, et al., *Staphylococcus aureus*: A Well-Armed Pathogen, Clin. Infect. Dis., 1998, 1179-1181, 26.
Baba, et al., Genome and virulence determinants of high virulence community-acquired MRSA, Lancet, 2000, 1819-1827, 359.
Berzofsky, et al., Strategies for designing and optimizing new generation vaccines, Nature Reviews, 2001, 209-219, 1.
Brady, et al., Identification of *Staphylococcus aureus* proteins recognized by the antibody-mediated immune response to a biofilm infection, Infect. Immun., 2006, 3415-3126, 74.
Brown, M. et al., Selection and characterization of murine monoclonal antibodies to *Staphylococcus aureus* iron-regulated surface determinant B with functional activity in vitro and in vivo., Clinical and Vaccine Immunology, 2009, 1095-1104, 16-8.

(Continued)

*Primary Examiner* — Gary Nickol
*Assistant Examiner* — Lakia Tongue
(74) *Attorney, Agent, or Firm* — Henry P. Wu; Gloria M. Fuentes

(57) ABSTRACT

The present invention relates to methods of inducing an immune response to *Staphylococcus* comprising administering a composition comprising an SA2451-related polypeptide from *Staphylococcus aureus* as well as derivatives or fragments thereof. The present invention also encompasses methods of treating and/or reducing the likelihood of a *Staphylococcus* infection by administering a composition comprising an SA2451-related polypeptide or an antibody that specifically binds to an SA2451 polypeptide, derivative or fragments thereof. Compositions administered in the methods of the invention can include one or more additional antigens. Compositions used to practice the methods of the invention are also encompassed.

6 Claims, 6 Drawing Sheets

(56) References Cited

FOREIGN PATENT DOCUMENTS

| WO | WO2006078680 | 7/2006 |
|---|---|---|
| WO | WO2007001361 | 1/2007 |
| WO | WO2010062814 | 6/2010 |
| WO | WO2010062815 | 6/2010 |
| WO | WO2012009247 | 1/2012 |
| WO | WO2012021229 | 2/2012 |

OTHER PUBLICATIONS

Clarke, et al., Identification of in vivo-expressed antigens of Staphylococcus aureus and their use in vaccinations for protection against nasal carriage, Journal of Infectious Disease, 2006, 1098-1108, 193.

Cook, J. et al., Staphylococcus aureus capsule type 8 antibodies provide inconsistent efficacy in murine models of staphylococcal infection., Human Vaccines, 2009, 254-263, 5.

Etz, et al., Identification of in vivo expressed vaccine candidate antigens from Staphylococcus aureus, PNAS, 2002, pp. 6573-6578, vol. 99, No. 10.

Gatlin, et al., Proteomic profiling of cell envelope-associated proteins from Staphylococcus aureus, Proteomics, 2006, 1530-1549, 6.

Gill, Steven R., Insights on Evolution of Virulence and Resistance from the Complete Genome Analysis of an Early Methicillin-Resistant Staphylococcus aureus Strain and a Biofilm-Producing Methicillin-Resistant Staphylococcus epidermidis Strain, Journal of Bacteriology, 2005, 2426-2438, 187-7.

Glowalla, E. et al., Proteomics-Based Identification of Anchorless Cell Wall Proteins as Vaccine Candidates against Staphylococcus aureus, Infection and Immunity, Jul. 1, 2009, 2719-2729, vol. 77, No. 7.

Josefsson, et al., Protection against Experimental Staphylococcus aureus Arthritis by Vaccination with Clumping Factor A, a Novel Virulence Determinant, Journal of Infectious Diseases, 2001, 1572-1580, 184.

Joyce, et al., Isolation, structural characterization, and immunological evaluation of a high-molecular-weight exopolysaccharide from Staphylococcus aureus, Carbohydrate Research, 2003, 903-922, 338.

Kristian, S.A. et al., D-Alanylation of Teichoic Acids Promotes Group A Streptococcus Antimicrobial Peptide Resistance, Neutrophil Survival, and Epithelial Cell Invasion, Journal of Bacteriology, 2005, 6719-6725, 187(19).

Kuklin, N.A. et al., A novel Staphylococcus aureus vaccine: iron surface determinant B induces rapid antibody responses in rhesus macaques and specific increased survival in a murine S. aureus sepsis model., Infection and Immunity, 2006, 2215-2223, 74.

Kuroda, et al., Whole genome sequencing of meticillin-resistant Staphylococcus aureus, Lancet, 2001, 1225-1240, 357.

Lowy, et al., Staphylococcus aureus infections, New England Journal of Medicine, 1998, 520-532, 339.

Mamo, et al., Vaccination with Staphylococcus aureus fibrinogen binding proteins (FgBPs) reduces colonisation of S. aureus in a mouse mastitis model, FEMS Immunol. Med. Mic., 1994, 47-54, 10.

Nandakumar, et al., Proteome analysis of membrane and cell wall associated proteins from Staphylococcus aureus, Proteome Res., 2005, 250-257, 4.

Nilsson, et al., Vaccination with a Recombinant Fragment of Collagen Adhesin Provides Protection against Staphylococcus aureus-mediated Septic Death, J. Clin. Invest., 1998, 2640-2649, 101.

Palazzo, et al., First report of vancomycin-resistant staphylococci isolated from healthy carriers in Brazil., J. Clin. Microbiol., 2005, 179-185, 43.

Peacock, et al., Methicillin-resistant Staphylococcus aureus: introduction and spread within a hospital, Annals of internal medicine, 1980, 526-532, 93.

Pieper, et al., Comparative proteomic analysis of Staphylococcus aureus strains with differences in resistance to the cell wall-targeting antibiotic vancomycin, Proteomics, 2006, 4246-4258, 6.

Selvey, et al., Nosocomial methicillin-resistant Staphylococcus aureus bacteremia: is it any worse than nosocomial methicillin-sensitive Staphylococcus aureus bacteremia?, Infect. Control. Hosp. Epidemiol., 2000, 645-648, 21.

Shinefield, et al., Use of a Staphylococcus aureus conjugate vaccine in patients receiving hemodialysis, N. Eng. J. Med., 2002, 491-496, 346.

Sivaraman et al., Pathogenesis gene families in the common minimal genome of Staphylococcus aureus are hypervariable, FEBS Letters, 2009, 1304-1308, 583:8.

Sivaraman Supplemental Information 2 document, online document retrieved on Dec. 13, 2012.

Sivaraman, et al., Genome Sequencing and analysis reveals possible determinants of Staphylococcus aureus nasal carriage, BMC Genomics, 2008, 1-13, 9:433.

Stranger-Jones, et al., Vaccine assembly from surface proteins of Staphylococcus aureus, Proc. Natl. Acad. Sci. USA, 2006, 16942-16947, 103.

Tenover, et al., Characterization of staphylococci with reduced susceptibilities to vancomycin and other glycopeptides, J. Clin. Microbiol., 1998, 1020-1027, 36.

Tenover, et al., Increasing resistance to vancomycin and other glycopeptides in Staphylococcus aureus, Emerg. Infect. Dis., 2001, 327-332, 7.

Vytvytska, et al., Identification of vaccine candidate antigens of Staphylococcus aureus by serological proteome analysis, Proteomics, 2002, 580-590, 2.

Weichhart, et al., Functional selection of vaccine candidate peptides from Staphylococcus aureus whole-genome expression libraries in vitro., Infect. Immun., 2003, 4633-4641, 71.

Yang, et al., A novel peptide isolated from phage library to substitute a complex system for a vaccine against staphylococci infection., Vaccine, 2006, 1117-1123, 24.

Sab, Peter; "Antibacterial treatment of Staphylococcus aureus: Response and resistance to the lantibiotic mersacidin and evaluation of endolysins as a biofilm treatment strategy"; Doctoral Dissertation, University of Bonn, 2008 (Retrieved from the Internet: URL:http://hss.ulb.uni-bonn.de/2009/1673/1673.pdf).

Uniprot Accession No. C8KK51, Glycine betaine/carnitine/choline ABC transporter opuCC, Sep. 21, 2011.

* cited by examiner

ATGAAGAAAATTAAATATATACTTGTCGTGTTTGTCTTATCGCTTACC
GTATTATCTGGATGTAGTTTGCCCGGACTAGGTAGTAAGAGCACGAA
AAATGATGTCAAAATTACAGCATTATCAACAAGCGAATCGCAAATTAT
TTCACATATGTTACGGTTGTTAATAGAGCATGATACACACGGTAAGA
TAAAGCCAACATTAGTAAATAATTTAGGGTCAAGTACGATTCAACATA
ATGCCTTAATTAATGGGGATGCTAATATATCAGGTGTTAGATATAATG
GCACAGATTTAACGGGAGCTTTGAAGGAAGCACCAATTAAAAATCCT
AAGAAAGCAATGATAGCAACACAACAAGGATTTAAAAAGAAATTTGA
TCAAACGTTTTTTGATTCGTATGGTTTTGCGAATACGTATGCATTCAT
GGTAACGAAGGAAACCGCTAAAAATATCATTTAGAGACAGTTTCAG
ATTTAGCAAAGCATAGTAAAGATTTACGTTTAGGTATGGATAGTTCAT
GGATGAATCGTAAAGGCGATGGCTATGAAGGATTTAAAAAGAGTAT
GGTTTTGACTTTGGTACAGTGAGACCAATGCAAATAGGTCTAGTCTA
CGACGCATTAAACTCAGAGAAGTTAGACGTTGCATTAGGTTAT
TCTACAGATGGTCGAATTGCGGCGTATGATTTGAAAGTACTTAAAGA
TGATAAACAATTTTTCCCACCTTATGCTGCGAGTGCTGTTGCAACAA
ATGAATTATTACGGCAACACCCAGAACTTAAAACGACGATTAATAAG
TTGACAGGAAAGATTTCGACTTCAGAGATGCAACGCTTGAATTATGA
AGCGGATGGTAAAGGTAAAGAACCTGCTGTCGTCGCAGAAGAATTT
TTGAAAAAACACCACTATTTTGATAAACAGAAGGTGGTCATAAGTAA
(SEQ ID NO:3)

FIG. 1

MKKIKYILVVFVLSLTVLSGCSLPGLGSKSTKNDVKITALSTSESQIISHML
RLLIEHDTHGKIKPTLVNNLGSSTIQHNALINGDANISGVRYNGTDLTGAL
KEAPIKNPKKAMIATQQGFKKKFDQTFFDSYGFANTYAFMVTKETAKKY
HLETVSDLAKHSKDLRLGMDSSWMNRKGDGYEGFKKEYGFDFGTVRP
MQIGLVYDALNSEKLDVALGYSTDGRIAAYDLKVLKDDKQFFPPYAASA
VATNELLRQHPELKTTINKLTGKISTSEMQRLNYEADGKGKEPAVVAEE
FLKKHHYFDKQKGGHK (SEQ ID NO:1)

FIG.2A

MKKIKYILVVFVLSLTVLSGCSLPGLGSKSTKNDVKITALSTSESQII
SHMLRLLIEHDTHGKIKPTLVNNLGSSTIQHNALINGDANISGVRY
NGTDLTGALKEAPIKNPKKAMIATQQGFKKKFDQTFFDSYGFANT
YAFMVTKETAKKYHLETVSDLAKHSKDLRLGMDSSWMNRKGDG
YEGFKKEYGFDFGTVRPMQIGLVYDALNSEKLDVALGYSTDGRIA
AYDLKVLKDDKQFFPPYAASAVATNELLRQHPELKTTINKLTGKIS
TSEMQRLNYEADGKGKEPAVVAEEFLKKHHYFDKQKGGHKHHH
HHHH* (SEQ ID NO:2)

FIG.2B

|  | Survival at 10 days post challenge | | |
|---|---|---|---|
| Test antigen | Exp 1 MSE#116 | Exp 2 MSE#120 | Total |
| SA2451 | 8/20 (40%) | 12/20 (60%) | 20/40 (50%) |
| BSA MAA | 2/20 (10%) | 5/20 (25%) | 7/40 (18%) |
| *P value | 0.0027 | 0.0250 | 0.0003 |

*log rank (Mantel–Cox)

FIG.3

SEQUENCE LISTING

```
<160> NUMBER OF SEQ ID NOS: 6

<210> SEQ ID NO 1
<211> LENGTH: 319
<212> TYPE: PRT
<213> ORGANISM: Staphylococcus aureus

<400> SEQUENCE: 1

Met Lys Lys Ile Lys Tyr Ile Leu Val Val Phe Val Leu Ser Leu Thr
1               5                   10                  15

Val Leu Ser Gly Cys Ser Leu Pro Gly Leu Gly Ser Lys Ser Thr Lys
            20                  25                  30

Asn Asp Val Lys Ile Thr Ala Leu Ser Thr Ser Glu Ser Gln Ile Ile
        35                  40                  45

Ser His Met Leu Arg Leu Leu Ile Glu His Asp Thr His Gly Lys Ile
    50                  55                  60

Lys Pro Thr Leu Val Asn Asn Leu Gly Ser Ser Thr Ile Gln His Asn
65                  70                  75                  80

Ala Leu Ile Asn Gly Asp Ala Asn Ile Ser Gly Val Arg Tyr Asn Gly
                85                  90                  95

Thr Asp Leu Thr Gly Ala Leu Lys Glu Ala Pro Ile Lys Asn Pro Lys
            100                 105                 110

Lys Ala Met Ile Ala Thr Gln Gln Gly Phe Lys Lys Lys Phe Asp Gln
        115                 120                 125

Thr Phe Phe Asp Ser Tyr Gly Phe Ala Asn Thr Tyr Ala Phe Met Val
    130                 135                 140

Thr Lys Glu Thr Ala Lys Lys Tyr His Leu Glu Thr Val Ser Asp Leu
145                 150                 155                 160

Ala Lys His Ser Lys Asp Leu Arg Leu Gly Met Asp Ser Ser Trp Met
                165                 170                 175

Asn Arg Lys Gly Asp Gly Tyr Glu Gly Phe Lys Lys Glu Tyr Gly Phe
            180                 185                 190

Asp Phe Gly Thr Val Arg Pro Met Gln Ile Gly Leu Val Tyr Asp Ala
        195                 200                 205

Leu Asn Ser Glu Lys Leu Asp Val Ala Leu Gly Tyr Ser Thr Asp Gly
    210                 215                 220

Arg Ile Ala Ala Tyr Asp Leu Lys Val Leu Lys Asp Asp Lys Gln Phe
225                 230                 235                 240

Phe Pro Pro Tyr Ala Ala Ser Ala Val Ala Thr Asn Glu Leu Leu Arg
                245                 250                 255

Gln His Pro Glu Leu Lys Thr Thr Ile Asn Lys Leu Thr Gly Lys Ile
            260                 265                 270

Ser Thr Ser Glu Met Gln Arg Leu Asn Tyr Glu Ala Asp Gly Lys Gly
```

```
            275                 280                 285
Lys Glu Pro Ala Val Val Ala Glu Glu Phe Leu Lys Lys His His Tyr
    290                 295                 300

Phe Asp Lys Gln Lys Gly Gly His Lys Ser Glu Gln Ile Asp Asn
305                 310                 315

<210> SEQ ID NO 2
<211> LENGTH: 327
<212> TYPE: PRT
<213> ORGANISM: Artificial Sequence
<220> FEATURE:
<223> OTHER INFORMATION: His-tagged SA2451

<400> SEQUENCE: 2

Met Lys Lys Ile Lys Tyr Ile Leu Val Phe Val Leu Ser Leu Thr
1               5                   10                  15

Val Leu Ser Gly Cys Ser Leu Pro Gly Leu Gly Ser Lys Ser Thr Lys
                20                  25                  30

Asn Asp Val Lys Ile Thr Ala Leu Ser Thr Ser Glu Ser Gln Ile Ile
            35                  40                  45

Ser His Met Leu Arg Leu Leu Ile Glu His Asp Thr His Gly Lys Ile
    50                  55                  60

Lys Pro Thr Leu Val Asn Asn Leu Gly Ser Ser Thr Ile Gln His Asn
65                  70                  75                  80

Ala Leu Ile Asn Gly Asp Ala Asn Ile Ser Gly Val Arg Tyr Asn Gly
                85                  90                  95

Thr Asp Leu Thr Gly Ala Leu Lys Glu Ala Pro Ile Lys Asn Pro Lys
            100                 105                 110

Lys Ala Met Ile Ala Thr Gln Gln Gly Phe Lys Lys Lys Phe Asp Gln
        115                 120                 125

Thr Phe Phe Asp Ser Tyr Gly Phe Ala Asn Thr Tyr Ala Phe Met Val
130                 135                 140

Thr Lys Glu Thr Ala Lys Lys Tyr His Leu Glu Thr Val Ser Asp Leu
145                 150                 155                 160

Ala Lys His Ser Lys Asp Leu Arg Leu Gly Met Asp Ser Ser Trp Met
                165                 170                 175

Asn Arg Lys Gly Asp Gly Tyr Glu Gly Phe Lys Lys Glu Tyr Gly Phe
            180                 185                 190

Asp Phe Gly Thr Val Arg Pro Met Gln Ile Gly Leu Val Tyr Asp Ala
        195                 200                 205

Leu Asn Ser Glu Lys Leu Asp Val Ala Leu Gly Tyr Ser Thr Asp Gly
    210                 215                 220

Arg Ile Ala Ala Tyr Asp Leu Lys Val Leu Lys Asp Asp Lys Gln Phe
225                 230                 235                 240

Phe Pro Pro Tyr Ala Ala Ser Ala Val Ala Thr Asn Glu Leu Leu Arg
                245                 250                 255

Gln His Pro Glu Leu Lys Thr Thr Ile Asn Lys Leu Thr Gly Lys Ile
            260                 265                 270

Ser Thr Ser Glu Met Gln Arg Leu Asn Tyr Glu Ala Asp Gly Lys Gly
        275                 280                 285

Lys Glu Pro Ala Val Val Ala Glu Glu Phe Leu Lys Lys His His Tyr
    290                 295                 300

Phe Asp Lys Gln Lys Gly Gly His Lys His His His His His His
305                 310                 315                 320

His Ser Glu Gln Ile Asp Asn
```

<210> SEQ ID NO 3
<211> LENGTH: 942
<212> TYPE: DNA
<213> ORGANISM: Staphylococcus aureus

<400> SEQUENCE: 3

```
atgaagaaaa ttaaatatat acttgtcgtg tttgtcttat cgcttaccgt attatctgga      60
tgtagtttgc ccggactagg tagtaagagc acgaaaaatg atgtcaaaat tacagcatta     120
tcaacaagcg aatcgcaaat tatttcacat atgttacggt tgttaataga gcatgataca     180
cacggtaaga taaagccaac attagtaaat aatttagggt caagtacgat tcaacataat     240
gccttaatta atggggatgc taatatatca ggtgttagat ataatggcac agatttaacg     300
ggagctttga aggaagcacc aattaaaaat cctaagaaag caatgatagc aacacaacaa     360
ggatttaaaa agaaatttga tcaaacgttt tttgattcgt atggttttgc gaatacgtat     420
gcattcatgg taacgaagga aaccgctaaa aaatatcatt tagagacagt ttcagattta     480
gcaaagcata gtaaagattt acgtttaggt atggatagtt catggatgaa tcgtaaaggc     540
gatggctatg aaggatttaa aaaagagtat ggttttgact ttggtacagt gagaccaatg     600
caaataggtc tagtctacga cgcattaaac tcagagaagt tagacgttgc attaggttat     660
tctacagatg gtcgaattgc ggcgtatgat ttgaaagtac ttaaagatga taacaatttt     720
ttcccacctt atgctgcgag tgctgttgca acaaatgaat tattacggca cacccagaa     780
cttaaaacga cgattaataa gttgacagga aagatttcga cttcagagat gcaacgcttg     840
aattatgaag cggatggtaa aggtaaagaa cctgctgtcg tcgcagaaga attttttgaaa    900
aaacaccact attttgataa acagaaaggt ggtcataagt aa                        942
```

<210> SEQ ID NO 4
<211> LENGTH: 47
<212> TYPE: DNA
<213> ORGANISM: Artificial Sequence
<220> FEATURE:
<223> OTHER INFORMATION: PCR Primer

<400> SEQUENCE: 4

```
caccatgaag aaaattaaat atatacttgt cgtgtttgtc ttatcgc                    47
```

<210> SEQ ID NO 5
<211> LENGTH: 49
<212> TYPE: DNA
<213> ORGANISM: Artificial Sequence
<220> FEATURE:
<223> OTHER INFORMATION: PCR Primer

<400> SEQUENCE: 5

```
tcagtggtgg tggtggtggt ggtggtgctt atgaccacct ttctgttta                  49
```

<210> SEQ ID NO 6
<211> LENGTH: 645
<212> TYPE: PRT
<213> ORGANISM: Staphylococcus aureus

<400> SEQUENCE: 6

```
Met Asn Lys Gln Gln Lys Glu Phe Lys Ser Phe Tyr Ser Ile Arg Lys
1               5                   10                  15
Ser Ser Leu Gly Val Ala Ser Val Ala Ile Ser Thr Leu Leu Leu Leu
            20                  25                  30
```

-continued

Met Ser Asn Gly Glu Ala Gln Ala Ala Glu Glu Thr Gly Gly Thr
            35                  40                  45

Asn Thr Glu Ala Gln Pro Lys Thr Glu Ala Val Ala Ser Pro Thr Thr
 50                  55                  60

Thr Ser Glu Lys Ala Pro Glu Thr Lys Pro Val Ala Asn Ala Val Ser
 65                  70                  75                  80

Val Ser Asn Lys Glu Val Glu Ala Pro Thr Ser Glu Thr Lys Glu Ala
                 85                  90                  95

Lys Glu Val Lys Glu Val Lys Ala Pro Lys Glu Thr Lys Glu Val Lys
                100                 105                 110

Pro Ala Ala Lys Ala Thr Asn Asn Thr Tyr Pro Ile Leu Asn Gln Glu
                115                 120                 125

Leu Arg Glu Ala Ile Lys Asn Pro Ala Ile Lys Asp Lys Asp His Ser
130                 135                 140

Ala Pro Asn Ser Arg Pro Ile Asp Phe Glu Met Lys Lys Lys Asp Gly
145                 150                 155                 160

Thr Gln Gln Phe Tyr His Tyr Ala Ser Ser Val Lys Pro Ala Arg Val
                165                 170                 175

Ile Phe Thr Asp Ser Lys Pro Glu Ile Glu Leu Gly Leu Gln Ser Gly
                180                 185                 190

Gln Phe Trp Arg Lys Phe Glu Val Tyr Glu Gly Asp Lys Lys Leu Pro
                195                 200                 205

Ile Lys Leu Val Ser Tyr Asp Thr Val Lys Asp Tyr Ala Tyr Ile Arg
210                 215                 220

Phe Ser Val Ser Asn Gly Thr Lys Ala Val Lys Ile Val Ser Ser Thr
225                 230                 235                 240

His Phe Asn Asn Lys Glu Glu Leu Tyr Asp Tyr Thr Leu Met Glu Phe
                245                 250                 255

Ala Gln Pro Ile Tyr Asn Ser Ala Asp Lys Phe Lys Thr Glu Glu Asp
                260                 265                 270

Tyr Lys Ala Glu Lys Leu Leu Ala Pro Tyr Lys Lys Ala Lys Thr Leu
                275                 280                 285

Glu Arg Gln Val Tyr Glu Leu Asn Lys Ile Gln Asp Lys Leu Pro Glu
290                 295                 300

Lys Leu Lys Ala Glu Tyr Lys Lys Lys Leu Glu Asp Thr Lys Lys Ala
305                 310                 315                 320

Leu Asp Glu Gln Val Lys Ser Ala Ile Thr Glu Phe Gln Asn Val Gln
                325                 330                 335

Pro Thr Asn Glu Lys Met Thr Asp Leu Gln Asp Thr Lys Tyr Val Val
                340                 345                 350

Tyr Glu Ser Val Glu Asn Asn Glu Ser Met Met Asp Thr Phe Val Lys
                355                 360                 365

His Pro Ile Lys Thr Gly Met Leu Asn Gly Lys Lys Tyr Met Val Met
370                 375                 380

Glu Thr Thr Asn Asp Asp Tyr Trp Lys Asp Phe Met Val Glu Gly Gln
385                 390                 395                 400

Arg Val Arg Thr Ile Ser Lys Asp Ala Lys Asn Asn Thr Arg Thr Ile
                405                 410                 415

Ile Phe Pro Tyr Val Glu Gly Lys Thr Leu Tyr Asp Ala Ile Val Lys
                420                 425                 430

Val His Val Lys Thr Ile Asp Tyr Asp Gly Gln Tyr His Val Arg Ile
                435                 440                 445

-continued

```
Val Asp Lys Glu Ala Phe Thr Lys Ala Asn Thr Asp Lys Ser Asn Lys
    450                 455                 460
Lys Glu Gln Gln Asp Asn Ser Ala Lys Lys Glu Ala Thr Pro Ala Thr
465                 470                 475                 480
Pro Ser Lys Pro Thr Pro Ser Pro Val Glu Lys Glu Ser Gln Lys Gln
                485                 490                 495
Asp Ser Gln Lys Asp Asp Asn Lys Gln Leu Pro Ser Val Glu Lys Glu
            500                 505                 510
Asn Asp Ala Ser Ser Glu Ser Gly Lys Asp Lys Thr Pro Ala Thr Lys
        515                 520                 525
Pro Thr Lys Gly Glu Val Glu Ser Ser Ser Thr Thr Pro Thr Lys Val
    530                 535                 540
Val Ser Thr Thr Gln Asn Val Ala Lys Pro Thr Thr Ala Ser Ser Lys
545                 550                 555                 560
Thr Thr Lys Asp Val Val Gln Thr Ser Ala Gly Ser Ser Glu Ala Lys
                565                 570                 575
Asp Ser Ala Pro Leu Gln Lys Ala Asn Ile Lys Asn Thr Asn Asp Gly
            580                 585                 590
His Thr Gln Ser Gln Asn Asn Lys Asn Thr Gln Glu Asn Lys Ala Lys
        595                 600                 605
Ser Leu Pro Gln Thr Gly Glu Glu Ser Asn Lys Asp Met Thr Leu Pro
    610                 615                 620
Leu Met Ala Leu Leu Ala Leu Ser Ser Ile Val Ala Phe Val Leu Pro
625                 630                 635                 640
Arg Lys Arg Lys Asn
                645
```

PROTECTIVE VACCINE BASED ON STAPHYLOCOCCUS AUREUS SA2451 PROTEIN

CROSS-REFERENCE TO RELATED APPLICATIONS

This application is a §371 national stage application of PCT/US2012/062019, international filing date of Oct. 26, 2012, which claims priority to U.S. Ser. No. 61/553,589, filed Oct. 31, 2011, which is herein incorporated by reference in its entirety.

FIELD OF THE INVENTION

The present invention relates to methods of inducing an immune response to *Staphylococcus* using an SA2451 protein from *Staphylococcus aureus* as well as derivatives or fragments thereof. The present invention also relates to a composition, particularly an *S. aureus* vaccine, comprising an SA2451 polypeptide, derivative or fragment thereof, alone or in combination with one or more additional immunogens, capable of inducing a protective immune response.

REFERENCE TO SEQUENCE LISTING SUBMITTED ELECTRONICALLY

The sequence listing of the present application is submitted electronically via EFS-Web as an ASCII formatted sequence listing with a file name "MRLIFD00051USPCT-SEQLIST-29APR2014.TXT", creation date of Apr. 28, 2014, and a size of 13.0 KB. This sequence listing submitted via EFS-Web is part of the specification and is herein incorporated by reference in its entirety.

BACKGROUND OF THE INVENTION

*Staphylococcus aureus* is a bacterial pathogen responsible for a wide range of diseases and conditions, ranging from minor skin infections to serious life-threatening wound infections, bacteraemia, endocarditis, pneumonia, osteomyelitis and toxic shock syndrome. While *S. aureus* commonly colonizes in the nose and skin of healthy humans, often causing only minor infections (e.g., pimples, boils), it can also cause systemic infections. Examples of diseases and conditions caused by *S. aureus* include bacteremia, infective endocarditis, folliculitis, furuncle, carbuncle, impetigo, bullous impetigo, cellulitis, botryomyosis, toxic shock syndrome, scalded skin syndrome, central nervous system infections, infective and inflammatory eye disease, osteomyelitis and other infections of joints and bones, and respiratory tract infections. (*The Staphylococci in Human Disease*, Crossley and Archer (eds.), Churchill Livingstone Inc. 1997; Archer, 1998, *Clin. Infect. Dis.* 26:1179-1181.)

*Staphylococcus aureus* is a nosocomial as well as a community-acquired pathogen which causes several diseases ranging from. See Lowy et al., 1998, *N. Engl. J. Med.* 339:520-32. The worldwide growing incidence of staphylococcal infections is strongly related to the increased use of surgical devices and a growing number of immunocompromised patients. The situation has become more serious since the increased use of antibiotics led to the emergence of methicillin-resistant *S. aureus* strains (MRSA). See Selvey et al., 2000, *Infect. Control. Hosp. Epidemiol.* 21:645-8; Peacock et al., 1980, *Ann. Intern. Med.* 93:526-32. Additionally, *S. aureus* isolates with reduced susceptibility to vancomycin, the antibiotic of choice against MRSA strains, were described in the lab as well as the clinic See Tenover et al., 2001, *Emerg. Infect. Dis.* 7:327-32; Tenover et al., 1998, *J. Clin. Microbiol.* 36:1020-7; Palazzo et al., 2005, *J. Clin. Microbiol.* 43:179-85. The rising emergence of multidrug-resistant staphylococci has led to a growing interest in the development of alternative approaches to prevent and treat staphylococcal infections.

Information concerning *S. aureus* polypeptide sequences has been obtained from sequencing the *S. aureus* genome. See Kuroda et al., 2001, *Lancet* 357:1225-1240; Baba et al., 2000, *Lancet* 359:1819-1827; Gill et al., 2005, *J. Bacteriol.* 187:2426-2438 and European Patent Publication EP 0 786 519. To some extent, bioinformatics has been employed in efforts to characterize polypeptide sequences obtained from genome sequencing. See, e.g., European Patent Publication EP 0 786 519 and U.S. Pat. No. 6,593,114.

Techniques such as those involving display technology and sera from infected patients have also been used in an effort to help identify genes coding for potential antigens. See, e.g., International Publication Nos. WO 01/98499 and WO 02/059148; and Etz et al., 2002, *Proc. Natl. Acad. Sci. USA* 99:6573-6578. Numerous staphylococcal surface proteins have been identified so far using recently adopted technologies, like proteomics (see Brady et al., 2006, *Infect. Immun.* 74:3415; Gatlin et al., 2006, *Proteomics* 6:1530; Pieper et al., 2006, *Proteomics* 6:4246; Vytvytska et al., 2002, *Proteomics* 2:580; Nandakumar et al., 2005, *J. Proteome Res.* 4:250) or protein selection methods based on expression libraries (see Clarke et al., 2006, *J. Infect. Dis.* 193:1098; Etz et al., 2002, *Proc. Natl. Acad Sci. USA* 99:6573-8; Weichhart et al., 2003, *Infect. Immun.* 71:4633; and Yang et al., 2006, *Vaccine* 24:1117).

Vaccines consisting of one or more antigenic determinants can provide protection against lethal challenge with *S. aureus* in mice. See Stranger-Jones et al., 2006, *Proc. Natl. Acad. Sci. USA* 103:16942-7 and Kuklin et al., 2006, *Infect. Immun.* 74:2215. Recombinantly expressed polypeptides can readily be made, purified, and formulated as vaccines. Additionally, recombinant proteins can be combined with additional components to make multicomponent polypeptide vaccines that induce a spectrum of immune responses. Despite this, there are no reported protein based vaccines for staphylococcal infections in humans or animals to date. Thus, there remains a need for immunogens that can provide protective immunity against Staphylococcal infections in human and/or animals.

SUMMARY OF THE INVENTION

It is shown herein that SA2451-related polypeptides can provide protective immunity against *S. aureus* infection in a relevant animal model system. Accordingly, one aspect of the invention provides a composition comprising an immunologically effective amount of a polypeptide that is at least 95% identical to a SA2451 polypeptide (represented by SEQ ID NO:1) or a fragment of the polypeptide and a pharmaceutically acceptable carrier. In embodiments of the invention, the polypeptide is not SEQ ID NO:1. In more preferred embodiments, the polypeptide is at least 98% identical to SEQ ID NO:1.

Also provided by the invention are compositions as described above, which further comprise one or more additional *S. aureus* antigens or one or more additional antigens from another Staph species, such a *S. epidermidis*. The compositions of the invention may further comprise an adjuvant.

The present invention is further related to a method of inducing a protective immune response in a patient against an S. aureus infection comprising the steps of administering to the patient an immunologically effective amount of any of the compositions or vaccines described herein. The compositions are administered to a patient in need thereof, wherein the patient is human or a non-human mammal such as a cow. In some embodiments of the methods described herein, the compositions are given to a patient who suffers from weakened immunity, has received a foreign body implant or is on renal dialysis.

Also provided by the invention is the use of a polypeptide that is at least 95% identical to SEQ ID NO:1 or a fragment of the polypeptide in the manufacture of a medicament for inducing a protective immune response in a patient against S. aureus infection or the use of the compositions herein for inducing protective immunity against S. aureus.

Further provided by the invention is a method of conferring passive immunity to S. aureus infection in a patient comprising administering to the patient one or more antibodies that specifically bind to a polypeptide of SEQ ID NO:1.

BRIEF DESCRIPTION OF THE DRAWINGS

FIG. 1 show the nucleotide sequence (SEQ ID NO:3) of SA2451 from S. aureus strain COL.

FIGS. 2A-2B show the amino acid sequences of SA2451 (SEQ ID NO:1) and SA2451 with a carboxy-terminal His-tag (SEQ ID NO:2), which was added to facilitate purification of the antigen.

FIG. 3 shows the results from two independent murine lethal challenge experiments, as described in Example 3. Balb/c mice were immunized with either SA2451 or BSA formulated on Merck aluminum adjuvant (MAA) (see EXAMPLE 2) and were challenged with S. aureus Becker.

DETAILED DESCRIPTION OF THE INVENTION

Figure 4A:
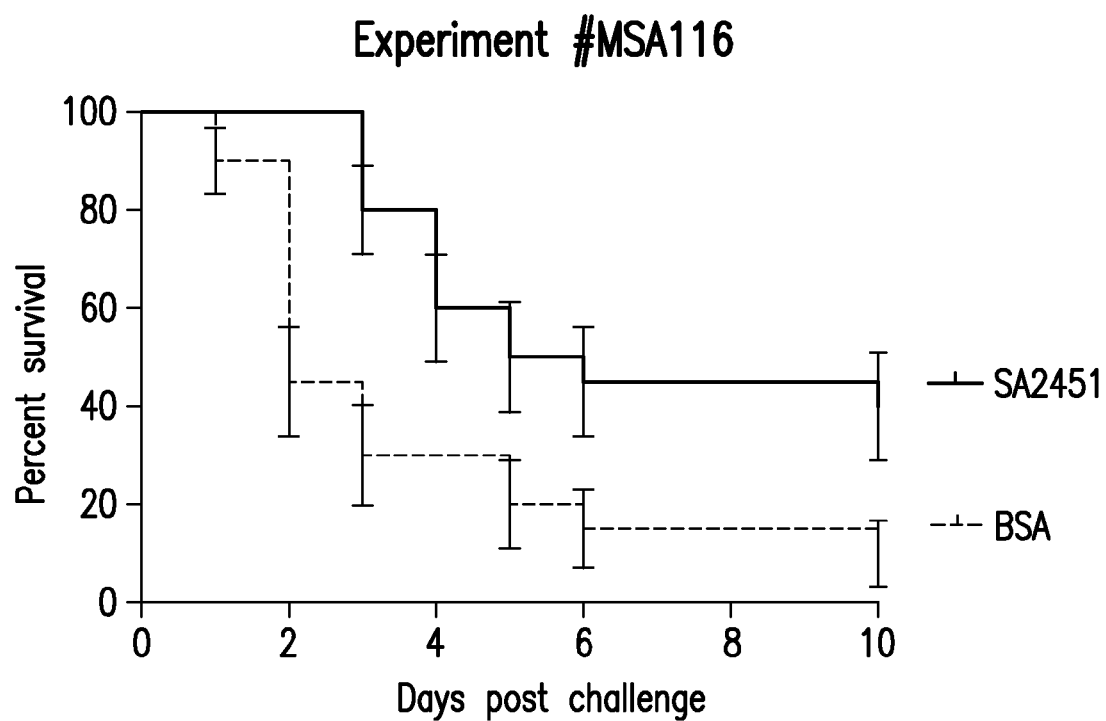
FIGS. 4A and 4B compare the survival curves from two independent murine lethal challenge experiments, as described in Example 3 (Experiments #MSA116 and MSA120). In each experiment, mice were immunized with either (a) His-tagged SA2451 adsorbed onto MAA or (b) BSA, which was also formulated with MAA, as described in Example 2, and challenged with S. aureus Becker.

As stated above, there is a need for the identification of S. aureus immunogens that can provide protective immunity against Staphylococcal infections. To that end, the present invention provides vaccines and methods of use thereof based on SA2451, which is an ABC transporter lipoprotein from S. aureus (Gill et al., 2005, J. Bacteriol. 187:2426-2438); known as glycine betaine/carnitine/choline transport system permease (ABC transporter protein), alternatively osmoprotectant binding protein (OpuCC). The ABC transporter family are diverse transmembrane proteins that utilize the energy of ATP hydrolysis to carry out certain biological processes including translocation of various substrates across membranes. The common feature of all ABC transporters is that they consist of two distinct domains, the transmembrane domain (TMD) and the nucleotide-binding domain (NBD) (Higgins, 1992, Annu. Rev. Cell Biol. 8:67).

SA2451 was originally identified for use as a potential immunogen in a Staph-based vaccine using a genomics approach. A conserved motif for Staphylococcus aureus lipoproteins was used to search the S. aureus genome database. Antigens with the conserved motif were selected for cloning. Without being bound by theory, it was thought that antigens possessing the conserved motif could have one end inserted into the bacterial cell membrane, and the other end extending through the cell wall to be surface exposed; thus making them potential vaccine targets.

SA2451 related sequences are disclosed in EP Patent Publication No. 786519, WO 02/094868, and US 2010/047267. However, no data is provided to demonstrate the usefulness of these sequences in a protective vaccine against S. aureus. In contrast, the inventors have shown herein that a His-tagged-derivative of SA2451 (SEQ ID NO:2) is able to provide protective immunity from challenge with S. aureus strain Becker in a murine model system; e.g. Balb/c mice. It is further shown herein that SA2451-related sequences (e.g. SEQ ID NO:2) can induce an immune response in rhesus monkeys. The vaccines of the present invention can provide protection against infection with S. aureus strains, e.g. strain Becker or strain COL.

A S. aureus SA2451 gene sequence was cloned from S. aureus strain COL and expressed recombinantly in E. coli. The recombinant protein is immunogenic in rodents and protects the animals from S. aureus infection. As used herein, the term "SA2451" refers to a polypeptide of SEQ ID NO:1 or a naturally occurring allelic variant or a homolog from another S. aureus strain. Examples of other strains of S. aureus include Becker, MW2, N315 (see Kuroda et al., 2001, Lancet 357:1225), Newman, USA300 (see Diep et al., 2006, Lancet 367:731), MSA817, and Mu3. In one embodiment, SA2451 is SEQ ID NO:1, which is from S. aureus strain COL. SA2451 may also be from another S. aureus strain. "SA2451-related sequences" refer to sequences that are highly identical to the SA2451 provided in SEQ ID NO:1, or derivatives or fragments thereof. Embodiments of the invention provide pharmaceutical compositions that comprise an immunologically effective amount of a SA2451 immunogen and a pharmaceutically acceptable carrier, wherein the SA2451 immunogen is not SEQ ID NO:1 and wherein the SA2451 immunogen is a polypeptide that is at least 95% identical to SEQ ID NO:1. SA2451 immunogens useful in the present invention are further defined, infra.

In one embodiment, SA2451 polypeptides, derivatives or fragments thereof are used as a vaccine for the treatment and/or reducing the likelihood of staphylococcal infections. Methods of the invention encompass administering a composition comprising a vaccine of the invention to a non-human animal or human patient in need thereof to induce an immune response. In a specific embodiment of the invention, one or more additional antigens are provided in the composition comprising an isolated SA2451 polypeptide, derivative or fragment thereof. In one embodiment, the additional antigen is IsdB (also known as ORF0657) or a derivative or fragment thereof.

As used herein, the phrase "induce an immune response" refers to the ability of a polypeptide, derivative, or fragment thereof to produce an immune response in a patient, preferably a mammal, to which it is administered, wherein the response includes, but is not limited to, the production of elements, such as antibodies, which specifically bind S. aureus or said polypeptide, derivative or fragment thereof.

The immune response provides a protective effect against *S. aureus* infection, ameliorates at least one pathology associated with *S. aureus* infection and/or reduces the likelihood that a patient will contract an *S. aureus* infection. In a specific embodiment, the immune response induces opsonophagocytic activity of human neutrophils for *S. aureus*.

As used herein, the phrase "an immunologically effective amount" refers to the amount of an immunogen that can induce a protective immune response against *S. aureus* when administered to a patient. The amount should be sufficient to significantly reduce the likelihood or severity of an *S. aureus* infection and/or the clinical manifestations thereof. Animal models known in the art can be used to assess the protective effect of administration of immunogen. For example, a murine, lethal-challenge model (see, e.g., Thakker et al., 1998, *Inf Immun* 66:5183-5189; Fattom et al., 1996, *Inf Immun* 64:1659-1665) and a rat, indwelling-catheter, sublethal challenge model (see, e.g., Ulphani et al., 1999, *Lab Animal Sc.* 49:283-287; Baddour et al., 1992, *J Inf Dis* 165:749-53; Ebert et al., *Human Vaccines* 7(6): 1-9 (2011)) can be used.

In another embodiment, SA2451 polypeptides, derivatives or fragments thereof are used as a target for generating antibodies. These antibodies can be administered to a patient for the treatment and/or reduction of the likelihood of staphylococcal infections due to passive immunity.

As used herein, the phrase "passive immunity" refers to the transfer of active humoral immunity in the form of antibodies. Passive immunity provides immediate protective effect to the patient from the pathogen recognized by the administered antibodies and/or ameliorates at least one pathology associated with pathogen infection. However, the patient does not develop an immunological memory to the pathogen and therefore must continue to receive the administered antibodies for protection from the pathogen to persist.

Embodiments of the invention also include one or more of the polypeptide immunogens or compositions thereof, described herein, or a vaccine comprising or consisting of said immunogens or compositions (i) for use in, (ii) for use as a medicament for, or (iii) for use in the preparation of a medicament for: (a) therapy (e.g., of the human body); (b) medicine; (c) inhibition of *S. aureus* replication; (d) treatment or prophylaxis of infection by *S. aureus*; or, (e) treatment, prophylaxis of, or delay in the onset or progression of *S. aureus*-associated disease(s), including, but not limited to: skin infections, wound infections, bacteremia, endocarditis, pneumonia, osteomyelitis, toxic shock syndrome, infective endocarditis, folliculitis, furuncle, carbuncle, impetigo, bullous impetigo, cellulitis, botryomyosis, scalded skin syndrome, central nervous system infections, infective and inflammatory eye disease, osteomyelitis and other infections of joints and bones, and respiratory tract infections. The polypeptide immunogens of the invention are also useful for treatment, prophylaxis of, or delay in the onset or progression of *S. aureus*-associated disease common to animals including: bovine mastitis, respiratory disease in swine, skeletal problems, and skin infections in companion animals such as horses, dogs and cats. In these uses, the polypeptide immunogens, compositions thereof, and/or vaccines comprising or consisting of said immunogens or compositions can optionally be employed in combination with one or more anti-bacterial agents (e.g., anti-bacterial compounds; combination vaccines, described infra).

Polypeptides

The amino acid sequence of a wild type full length SA2451 from *S. aureus* subsp. *aureus* COL is SEQ ID NO:1. SEQ ID NO:1 as well as derivatives and fragments thereof can be used in the methods of the invention. Collectively, derivatives and fragments of SEQ ID NO:1 are termed "altered polypeptides" or "SA2451-related sequence". SEQ ID NO:2 is a His-tagged derivative of SEQ ID NO:1 which was shown herein to provide protective immunity against *S. aureus* infections in animal model systems.

As used herein, the term "isolated" indicates a different form than found in nature. The different form of the polypeptide can be, for example, a different purity than found in nature. In one embodiment, the term refers to polypeptides that are substantially or essentially free from components that normally accompany it in its native state.

As used herein, the terms "purified" with regard to, for example, a polypeptide immunogen indicates the presence of such polypeptide in an environment lacking one or more other polypeptides with which it is naturally associated and/or is represented by at least about 10% of the total protein present. In different embodiments, the purified polypeptide represents at least about 50%, at least about 75%, at least about 95%, or at least about 99% of the total protein in a sample or preparation.

As used herein, the term "fragment" refers to a continuous segment of an SA2451 polypeptide (i.e., SEQ ID NO:1) or derivatives thereof having at least 5 amino acid residues, at least 10 amino acid residues, at least 15 amino acid residues, or at least 20 amino acid residues and which is shorter than the full length SA2451 polypeptide. Preferably, fragments will comprise at least one antigenic determinant or epitopic region. In some embodiments, a fragment of the invention will comprise a domain of the SA2451 polypeptide including, but not limited to, the extracellular domain or T cell epitopes (either from the intracellular or extracellular portion of SA2451). One or more fragments comprising at least one antigenic determinant or epitopic region may be fused together.

As used herein, the terms "epitope" or "antigenic determinant" refer to a site on an antigen to which an antibody and/or T cell receptor binds. Epitopes can be formed both from contiguous amino acids or noncontiguous amino acids juxtaposed by tertiary folding of a protein. Epitopes formed from contiguous amino acids are typically retained on exposure to denaturing solvents whereas epitopes formed by tertiary folding are typically lost on treatment with denaturing solvents. An epitope typically includes at least 3, and more usually, at least 5 or 8-10 amino acids in a unique spatial conformation. Methods of determining spatial conformation of epitopes include, for example, x-ray crystallography and 2-dimensional nuclear magnetic resonance.

As used herein, the term "derivative" refers to a polypeptide having one or more alterations, which can be changes in the amino acid sequence (including additions and deletions of amino acid residues) and/or chemical modifications. In preferred embodiments, the derivative is at least 85%, at least 90%, at least 95%, at least 97%, at least 99% identical to the original sequence prior to alteration. In some preferred embodiments, the polypeptide is not SEQ ID NO:1. In general, derivatives retain the activity of inducing a protective immune response. In some embodiments, SA2451 or a fragment thereof has been altered to a derivative of the invention such that one or more epitopes have been enhanced. Epitope enhancement improves the efficacy of a polypeptide to induce a protective immune response. Epitope enhancement can be performed using different techniques such as those involving alteration of anchor residues to improve peptide affinity for MHC molecules and those that increase the affinity of the peptide-MHC complex for a T-cell receptor (Berzofsky et al., 2001, *Nature Review* 1:209-219).

In one embodiment, a derivative is a polypeptide that has an amino acid sequence which differs from the base sequence from which it is derived by one or more amino acid substitutions. Amino acid substitutions may be regarded as "conservative" where an amino is replaced with a different amino acid with broadly similar properties. "Non-conservative" substitutions are where amino acids are replaced with amino acids of a different type. Broadly speaking, fewer non-conservative substitutions will be possible without altering the biological activity of the polypeptide. In some embodiments, no more than 12 amino acid residues, 11 amino acid residues, 10 amino acid residues, 9 amino acid residues, 8 amino acid residues, 7 amino acid residues, 6 amino acid residues, 5 amino acid residues, 4 amino acid residues, 3 amino acid residues, 2 amino acid residues, or 1 amino acid residue is/are substituted.

In another embodiment, a derivative is a polypeptide that has an amino acid sequence which differs from the base sequence from which it is derived by having one or more amino acid deletions and/or additions in any combination. Deleted or added amino acids can be either contiguous or individual residues. In some embodiments, no more than 25 amino acid residues, no more than 20 amino acid residues, no more than 15 amino acid residues, no more than 12 amino acid residues, no more than 10 amino acid residues, no more than 8 amino acid residues, no more than 7 amino acid residues, no more than 6 amino acid residues, no more than 5 amino acid residues, no more than 4 amino acid residues, no more than 3 amino acid residues, no more than 2 amino acid residues, or no more than 1 amino acid residue is/are deleted or added. In additional embodiments, domains of SA2412 including, but not limited to, the transmembrane domain, are deleted. Addition of amino acids may include fusion (either directly or via a linker) to at least one functional protein domain including, but not limited to, marker polypeptides, carrier polypeptides (including, but not limited to, OMPC, BSA, OVA, THY, KLH, tetanus toxoid, HbSAg, HBcAg, rotavirus capsid proteins, L1 protein of the human papilloma virus, diphtheria toxoid CRM197 protein, flagellin and HPV VLP especially type 6, 11 and 16), polypeptides holding adjuvant properties or polypeptides that assist in purification. Additionally, it will be appreciated that the additional amino acid residues can be derived from *S. aureus* or an unrelated source and may produce an immune response effective against *S. aureus* or another pathogen.

In another embodiment, a derivative is a polypeptide that has an amino acid sequence which differs from the base sequence from which it is derived by having one or more chemical modifications of the protein. Chemical modifications include, but are not limited to, modification of functional groups (such as alkylation, hydroxylation, phosphatation, thiolation, carboxilation and the like), incorporation of unnatural amino acids and/or their derivatives during protein synthesis and the use of crosslinkers and other methods which impose conformational constraints on the polypeptides.

Any method known in the art can be used to determine the degree of difference between SA2451 (e.g., SEQ ID NO:1) and a derivative. In one embodiment, sequence identity is used to determine relatedness. Derivatives of the invention will be at least 85% identical, at least 90% identical, at least 95% identical, at least 97% identical, at least 99% identical to the base sequence (e.g., SEQ ID NO:1). The percent identity is defined as the number of identical residues divided by the total number of residues and multiplied by 100. If sequences in the alignment are of different lengths (due to gaps or extensions), the length of the longest sequence will be used in the calculation, representing the value for total length.

In another embodiment, hybridization is used to determine relatedness. Nucleic acids encoding derivatives of the invention will hybridize to nucleic acids encoding SA2451 (e.g., SEQ ID NO:3) under highly stringent conditions. Stringency of hybridization reactions is readily determinable by one of ordinary skill in the art, and generally is an empirical calculation dependent upon probe length, washing temperature, and salt concentration. In general, longer probes require higher temperatures for proper annealing, while shorter probes need lower temperatures. Hybridization generally depends on the ability of denatured DNA to re-anneal when complementary strands are present in an environment below their melting temperature. The higher the degree of desired homology between the probe and hybridizable sequence, the higher the relative temperature which can be used. As a result, it follows that higher relative temperatures would tend to make the reaction conditions more stringent, while lower temperatures less so. Generally, stringent conditions are selected to be about 5° C. lower than the thermal melting point (Tm) for the specific sequence at a defined ionic strength and pH. The Tm is the temperature (under defined ionic strength, pH and nucleic acid concentration) at which 50% of the probes complementary to the target sequence hybridize to the target sequence at equilibrium. Since target sequences are generally present at excess, at Tm, 50% of the probes are occupied at equilibrium. Typically, stringent conditions will be those in which the salt concentration is less than about 1.0 M sodium ion, typically about 0.01 to 1.0 M sodium ion (or other salts) at pH 7.0 to 8.3; and the temperature is at least about 30° C. for short probes, primers or oligonucleotides (e.g., 10 to 50 nucleotides) and at least about 60° C. for longer probes, primers and oligonucleotides. Stringent conditions may also be achieved with the addition of destabilizing agents, such as formamide. For additional details and explanation of stringency of hybridization reactions, see Ausubel et al., Current Protocols in Molecular Biology, Wiley Interscience Publishers, (1995).

As used here, the phrase "high stringency" refers to conditions that: (1) employ low ionic strength and high temperature for washing, for example 0.015 M sodium chloride/0.0015 M sodium citrate, 0.1% SDS at 50° C.; (2) employ a denaturing agent, such as formamide, during hybridization for example, 50% (v/v) formamide with 0.1% BSA, 0.1% Ficoll, 0.1% polyvinylpyrrolidone, 50 mM sodium phosphate buffer at pH 6.5 with 750 mM sodium chloride/50 mM sodium citrate at 42° C.; or (3) employ 50% formamide, 5×SSC, 50 mM sodium phosphate (pH 6.8), 0.1% sodium pyrophosphate, 5×Denhardt's solution, sonicated salmon sperm DNA (50 μg/ml), 0.1% SDS, and 10% dextran sulfate at 42° C., with washes at 42° C. in 0.2×SSC and at 55° C. in 50% formamide, followed by a high-stringency wash consisting of 0.1×SSC containing EDTA at 55° C.

Polypeptide Production

The polypeptides, derivatives or fragments thereof for use in the methods of the invention can be produced recombinantly and, if needed, chemically modified. Recombinant expression of a polypeptide requires construction of an expression vector containing a polynucleotide that encodes the polypeptide of interest (i.e., an SA2451 polypeptide, derivative or fragment thereof). Once a polynucleotide encoding the polypeptide of interest has been obtained, the vector for the production of the polypeptide of interest may be produced by recombinant DNA technology using techniques well known in the art. Thus, methods for preparing a polypeptide of interest by expressing a polynucleotide encoding said polypeptide are described herein.

Methods which are well known to those skilled in the art can be used to construct expression vectors containing the coding sequences of the polypeptide of interest and appropriate transcriptional and translational control signals. These methods include, for example, in vitro recombinant DNA techniques, synthetic techniques, and in vivo genetic recombination. The invention, thus, provides replicable vectors comprising a nucleotide sequence encoding a polypeptide of interest operably linked to a promoter.

The expression vector is transferred to a host cell by conventional techniques and the transfected cells are then cultured by conventional techniques to produce the polypeptide of interest. Thus, the invention includes host cells containing a polynucleotide encoding a polypeptide of interest operably linked to a heterologous promoter.

A variety of host-expression vector systems may be utilized to express the polypeptides of interest. Such host-expression systems represent vehicles by which the coding sequences of interest may be produced and subsequently purified, but also represent cells which may, when transformed or transfected with the appropriate nucleotide coding sequences, express the polypeptide of interest in situ. These include but are not limited to microorganisms such as bacteria (e.g., *E. coli*, members of the *Staphylococcus* genus, such as *S. aureus* and *S. epidermidis*; members of the *Lactobacillus* genus, such as *L. plantarum*; members of the *Lactococcus* genus, such as *L. lactis*; members of the *Bacillus* genus, such as *B. subtilis*; members of the *Corynebacterium* genus such as *C. glutamicum*; and members of the *Pseudomonas* genus such as *Ps. fluorescens*.) transformed with recombinant bacteriophage DNA, plasmid DNA or cosmid DNA expression vectors containing coding sequences of interest; yeast (e.g., *Saccharomyces* genus such as *S. cerevisiae* or *S. pichia*, members of the *Pichia* genus such as *P. pastoris*, members of the *Hansenula* genus such as *H. polymorpha*, members of the *Kluyveromyces* genus such as *K. lactis* or *K. fragilis*, and members of the *Schizosaccharomyces* genus such as *S. pombe*) transformed with recombinant yeast expression vectors containing coding sequences of interest; insect cell systems infected with recombinant virus expression vectors (e.g., baculovirus) containing coding sequences of interest; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing coding sequences of interest; or mammalian cell systems (e.g., COS, CHO, BHK, 293, NSO, and 3T3 cells) harboring recombinant expression constructs containing promoters derived from the genome of mammalian cells (e.g., metallothionein promoter) or from mammalian viruses (e.g., the adenovirus late promoter; the vaccinia virus 7.5K promoter) and coding sequences of interest.

In addition, a host cell strain may be chosen which modulates the expression of the inserted sequences, or modifies and processes the gene product in the specific fashion desired. Eukaryotic modifications may include glycosylation and processing (e.g., cleavage) of protein products. Different host cells have characteristic and specific mechanisms for the post-translational processing and modification of proteins and gene products. Appropriate cell lines or host systems can be chosen to ensure the correct modification and processing of the foreign protein expressed. To this end, host cells which possess the cellular machinery for proper processing of the primary transcript, glycosylation, and phosphorylation of the gene product may be used. As used herein, the terms "polypeptide" or "an amino acid sequence of a polypeptide" includes polypeptides containing one or more amino acids having a structure of a post-translational modification from a host cell, such as a yeast host.

Once a polypeptide of interest has been produced by recombinant expression, it may be purified by different methods, for example, by chromatography (e.g., ion exchange, affinity, sizing column chromatography), centrifugation, differential solubility, or by any other standard technique for the purification of proteins. Further, the polypeptides of interest may be fused or attached to heterologous polypeptide sequences described herein or otherwise known in the art to facilitate purification. Examples of such protein tags include, but are not limited to, chitin binding protein (CBP), maltose binding protein (MBP), glutathione-S-transferase (GST), poly-histidine, hemagglutinin (HA) and poly-anionic amino acids.

If desired, expression in a particular host can be enhanced through codon optimization. Codon optimization includes use of more preferred codons. Techniques for codon optimization in different hosts are well known in the art.

Determination of Immunoreactive Derivatives and Fragments

The invention also extends to a method of identifying an immunoreactive derivative or fragments (collectively "altered polypeptides") of an SA2451 polypeptide. This method essentially comprises generating a derivative or fragment of the polypeptide, administering the altered polypeptide to a mammal; and detecting an immune response in the mammal. Such response will include production of elements which specifically bind *S. aureus* and/or said polypeptide, derivative or fragment and/or have a protective effect against *S. aureus* infection. Antibody titers and immunoreactivity against the native or parent polypeptide may then be determined by, for example, radioimmunoassay, ELISA, western blot or ELISPOT.

Adjuvants

Adjuvants are substances that can assist an immunogen (e.g., a polypeptide, pharmaceutical composition containing a polypeptide) in producing an immune response. Adjuvants can function by different mechanisms such as one or more of the following: increasing the antigen biologic or immunologic half-life; improving antigen delivery to antigen-presenting cells; improving antigen processing and presentation by antigen-presenting cells; and, inducing production of immunomodulatory cytokines (Vogel, *Clinical Infectious Diseases* 30 (suppl. 3): S266-270, 2000). In one embodiment of the present invention, an adjuvant is used.

A variety of different types of adjuvants can be employed to assist in the production of an immune response. Examples of particular adjuvants include aluminum hydroxide; aluminum phosphate, aluminum hydroxyphosphate, amorphous aluminum hydroxyphosphate sulfate adjuvant (AAHSA) or other salts of aluminum; calcium phosphate; DNA CpG motifs; monophosphoryl lipid A; cholera toxin; *E. coli* heat-labile toxin; pertussis toxin; muramyl dipeptide; Freund's incomplete adjuvant; MF59; SAF; immunostimulatory complexes; liposomes; biodegradable microspheres; saponins; nonionic block copolymers; muramyl peptide analogues; polyphosphazene; synthetic polynucleotides; IFN-γ; IL-2; IL-12; and ISCOMS. (Vogel, *Clinical Infectious Diseases* 30 (suppl 3): S266-270, 2000; Klein et al., 2000, *Journal of Pharmaceutical Sciences* 89:311-321; Rimmelzwaan et al., 2001, *Vaccine* 19:1180-1187; Kersten, 2003, *Vaccine* 21:915-920; O'Hagen, 2001, *Curr. Drug Target Infect. Disord.* 1:273-286.)

Combination Vaccines

An SA2451 polypeptide, derivative or fragment thereof can be used alone, or in combination with other immunogens, to induce an immune response. Additional immunogens that may be present include one or more additional *S. aureus* immunogens, one or more immunogens targeting one or more other *Staphylococcus* organisms such as *S. epidermidis*, *S. haemolyticus*, *S. warneri*, *S. pyogenes*, or *S. lugunensi*, and/or one or more immunogens targeting other infectious organisms including, but not limited to, the pathogenic bacteria *H. influenzae*, *M. catarrhalis*, *N. gonorrhoeae*, *E. coli*, *S. pneumoniae*, *C. difficile*, *C. perfringens*, *C. tetani*, bacteria of the genuses *Klebsiella*, *Serratia*, *Enterobacter*, *Proteus*, *Pseudomonas*, *Legionella*, and *Citrobacter*.

In one embodiment, the additional immunogen is IsdB (also known as ORF0657) or related polypeptides. Reference to an IsdB immunogen refers to an immunogen that produces a protective immune response that recognizes the IsdB protein in *S. aureus*. In different embodiments, the IsdB immunogen produces an immune response that recognizes IsdB present on one or more of the following strains: COL, Becker, MW2, N315, Newman, USA300, MSA817, and Mu3. The ability of an IsdB immunogen to provided protective immunity is illustrated in, for example, US Publication No. 2006/0177462 (which is incorporated by reference herein in its entirety).

In additional embodiments, the IsdB immunogen comprises a polypeptide region, said region (a) is at least 90%, at least 94%, at least 95% or at least 99% identical to SEQ ID NO:6 or a fragment thereof (including, but not limited to, amino acids 42-486, 42-522 and 42-608 of SEQ ID NO:6); (b) differs from SEQ ID NO:6 or a fragment thereof (including, but not limited to, amino acids 42-486, 42-522 and 42-608 of SEQ ID NO:6) by 0, 1, 2, 3, 4, 5, 6, 7, 8, 9, 10, 11, 12, 13, 14, 15, 16, 17, 18, 19, 20, 21, 22, 23, 24, or 25 alterations, or up to 50 alterations; or (c) consists essentially or consists of SEQ ID NO:6 or a fragment thereof (including, but not limited to, amino acids 42-486, 42-522 and 42-608 of SEQ ID NO:6). Examples of alterations include amino acid substitutions, deletions, and insertions.

Reference to "consists essentially" of indicated amino acids indicates that the referred to amino acids are present and additional amino acids may be present. The additional amino acids can be at the carboxyl or amino terminus. In different embodiments 1, 2, 3, 4, 5, 6, 7, 8, 9, 10, 11, 12, 13, 14, 15, 16, 17, 18, 19, or 20 additional amino acids are present. In preferred embodiments methionine is present at the amino terminus; or methionine-glycine is present at the amino terminus.

In other embodiments, the one or more additional immunogens include, but are not limited to, ORF0657/ORF0190 hybrid polypeptides (International Publication No. WO 05/009378 and US Publication No. 2006/0188515); ORF0688-related polypeptides; ORF0452-related polypeptides (US Publication 2008/131447); *S. epidermidis* ORF1319E-related polypeptides (WO 08/140632); *S. epidermidis* ORF2695E-related polypeptides (WO 08/115415); ORF0912-related polypeptides; ORF1902-related polypeptides; sai-1-related polypeptides (International Publication No. WO 05/79315); ORF0594-related polypeptides (International Publication No. WO 05/086663); ORF0826-related polypeptides (International Publication No. WO 05/115113); PBP4-related polypeptides (International Publication No. WO 06/033918); AhpC-related polypeptides and AhpC-AhpF compositions (International Publication No. WO 06/078680); PBP4-related polypeptides (WO06/033918); SACOL1902-related polypeptides (WO 10/062814); SACOL0912-related polypeptides (WO 10/062815); SA0024-related polypeptides (WO 07/001361); SACOL 2451-related polypeptides; SACOL2412-related polypeptides (PCT/US11/43499), SACOL1789-related polypeptides (PCT/US11/43274), SA2074-related polypeptides; *S. aureus* type 5 and type 8 capsular polysaccharides (Shinefield et al., 2002, *N. Eng. J. Med.* 346:491-496); collagen adhesin, fibrinogen binding proteins, and clumping factor (Mamo et al., 1994, *FEMS Immunol. Med. Microbiol.* 10:47-54; Nilsson et al., 1998, *J. Clin. Invest.* 101:2640-2649; Josefsson et al., 2001, *J. of Infect. Dis.* 184:1572-1580); and polysaccharide intercellular adhesin and fragments thereof (Joyce et al., 2003, *Carbohydrate Research* 338:903-922).

Nucleic Acid Vaccine

The nucleic acid sequence of wild type full length SA2451 from *S. aureus* subsp. *aureus* COL is SEQ ID NO:3 (FIG. 1C). SEQ ID NO:3 or other nucleic acids that encode an SA2451 polypeptide of SEQ ID NO:1, derivative or fragment thereof can be introduced into a patient using vectors suitable for therapeutic administration. Suitable vectors can deliver the nucleic acid into a target cell without causing an unacceptable side effect. Examples of vectors that can be employed include plasmid vectors and viral based vectors. (Barouch, 2006, *J. Pathol.* 208:283-289; Emini et al., International Publication No. WO 03/031588.)

Cellular expression is achieved using a gene expression cassette encoding the desired polypeptide. The gene expression cassette contains regulatory elements for producing and processing a sufficient amount of nucleic acid inside a target cell to achieve a beneficial effect.

Examples of viral vectors include first and second generation adenovectors, helper dependent adenovectors, adeno-associated viral vectors, retroviral vectors, alphavirus vectors (e.g., Venezuelan Equine Encephalitis virus vectors), and plasmid vectors. (Hitt a al., 1997, *Advances in Pharmacology* 40:137-206; Johnston et al., U.S. Pat. No. 6,156,588; Johnston et al., International PCT Publication no. WO 95/32733; Barouch, 2006, *J. Pathol.* 208:283-289; Emini et al., International PCT Publication no. WO 03/031588.)

Adenovectors can be based on different adenovirus serotypes such as those found in humans or animals. Examples of animal adenoviruses include bovine, porcine, chimpanzee, murine, canine, and avian (CELO). (Emini et al., International PCT Publication no. WO 03/031588; Colloca et al., International PCT Publication no. WO 05/071093.) Human adenovirus include Group B, C, D, or E serotypes such as type 2 ("Ad2"), 4 ("Ad4"), 5 ("Ad5"), 6 ("Ad6"), 24 ("Ad24"), 26 ("Ad26"), 34 ("Ad34") and 35 ("Ad35").

Nucleic acid vaccines can be administered using different techniques and dosing regimes (see, e.g., International Publication No. WO 03/031588 and U.S. Pat. No. 7,008,791). For example, the vaccine can be administered intramuscular by injection with or without one or more electric pulses. Electric mediated transfer can assist genetic immunization by stimulating both humoral and cellular immune responses. Examples of dosing regimes include prime-boost and heterologous prime-boost approaches.

SA2451 Antibodies

An SA2451 polypeptide, derivative or fragment thereof can be used to generate antibodies and antibody fragments that bind to SA2451 or to *S. aureus*. Such antibodies and antibody fragments can be used in polypeptide purification, *S. aureus* identification, and/or in therapeutic treatment of *S. aureus* infection. In preferred embodiments, antibodies and/or antibody fragments thereof are administered to a patient in need thereof to provide passive immunity to *S. aureus*.

As used herein, the term "antibody" as used includes monoclonal antibodies, polyclonal antibodies, multispecific antibodies (e.g. bispecific antibodies), single-chain Fvs (scFv) (including bi-specific scFvs), single chain antibodies, Fab fragments, F(ab') fragments, disulfide-linked Fvs (sdFv), and epitope-binding fragments of any of the above, so long as they exhibit the desired biological activity. In preferred embodiments, antibodies of the invention are monoclonal. In a more preferred embodiment, the monoclonal antibodies used in the methods of the invention are humanized or human antibodies.

As used herein, the term "monoclonal antibody" refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to polyclonal antibody preparations which typically include different antibodies directed against different determinants (epitopes), each monoclonal antibody is directed against a single determinant on the antigen. The monoclonal antibodies to be used in accordance with the present invention may be made by the hybridoma method first described by Kohler and Milstein, *Nature* 256, 495 (1975), or may be made by recombinant methods, e.g., as described in U.S. Pat. No. 4,816,567. The monoclonal antibodies for use with the present invention may also be isolated from phage antibody libraries using the techniques described in Clackson et al. *Nature* 352: 624-628 (1991), as well as in Marks et al., *J. Mol. Biol* 222: 581-597 (1991).

"Humanized" forms of non-human (e.g., murine) antibodies are immunoglobulins, immunoglobulin chains or fragments thereof (such as Fv, Fab, Fab', F(ab')$_2$ or other antigen-binding subsequences of antibodies) which contain minimal sequence derived from non-human immunoglobulin. For the most part, humanized antibodies are human immunoglobulins (recipient antibody) in which residues from a complementarity-determining region (CDR) of the recipient are replaced by residues from a CDR of a non-human species (donor antibody) such as mouse, rat or rabbit having the desired specificity, affinity, and capacity. Thus, a humanized antibody is a recombinant protein in which the CDRs from an antibody from one species; e.g., a rodent antibody, is transferred from the heavy and light variable chains of the rodent antibody into human heavy and light variable domains. The constant domains of the antibody molecule are derived from those of a human antibody. In some instances, Fv framework region (FR) residues of the human immunoglobulin are replaced by corresponding non-human residues. Furthermore, humanized antibodies may comprise residues which are found neither in the recipient antibody nor in the imported CDR or framework sequences. These modifications are made to further refine and optimize humanized antibody performance. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin sequence. The humanized antibody optimally also will comprise at least a portion of an immunoglobulin constant region (Fc), typically that of a human immunoglobulin (see, e.g., Yamashita et al., 2007, *Cytotech.* 55:55; Kipriyanov and Le Gall, 2004, *Mol. Biotechnol.* 26:39 and Gonzales et al., 2005, *Tumour Biol.* 26:31).

Completely human antibodies may be desirable for therapeutic treatment of human patients. Human antibodies can be made by a variety of methods known in the art including phage display methods described above using antibody libraries derived from human immunoglobulin sequences. See U.S. Pat. Nos. 4,444,887 and 4,716,111; and PCT publications WO 98/46645; WO 98/50433; WO 98/24893 and WO 98/16654, each of which is incorporated herein by reference in its entirety. Human antibodies can also be produced using transgenic mice which are incapable of expressing functional endogenous immunoglobulins, but which can express human immunoglobulin genes. See, e.g., PCT publications WO 98/24893; European Patent No. 0 598 877; U.S. Pat. Nos. 5,916,771; and 5,939,598, which are incorporated by reference herein in their entireties.

In some embodiments, Fc engineered variants antibodies of the invention are also encompassed by the present invention. Such variants include antibodies or antigen binding fragments thereof which have been engineered so as to introduce mutations or substitutions in the Fc region of the antibody molecule so as to improve or modulate the effector functions of the underlying antibody molecule relative to the unmodified antibody. In general, improved effector functions refer to such activities as CDC, ADCC and antibody half life (see, e.g., U.S. Pat. Nos. 7,371,826; 7,217,797; 7,083,784; 7,317,091; and 5,624,821, each of which is incorporated herein in its entirety).

There are five classes of immunoglobulins: IgA, IgD, IgE, IgG, and IgM. The IgG and IgA classes are further divided into subclasses on the basis of relatively minor differences in the constant heavy region sequence and function, e.g., humans express the following subclasses: IgG1, IgG2, IgG3, IgG4, IgA1, and IgA2. In preferred embodiments, the antibodies of the invention are IgG1.

Proper glycosylation can be important for antibody function (Yoo et al., 2002, *J. Immunol. Methods* 261:1-20; Li et al., 2006, *Nature Biotechnol.* 24:210-215). Naturally occurring antibodies contain at least one N-linked carbohydrate attached to a heavy chain (Yoo et al., supra). Additional N-linked carbohydrates and O-linked carbohydrates may be present and may be important for antibody function Id.

Different types of host cells can be used to provide for efficient post-translational modifications including mammalian host cells and non-mammalian cells. Examples of mammalian host cells include Chinese hamster ovary (Cho), HeLa, C6, PC 12, and myeloma cells (Yoo et al., supra; Persic et al., 1997, *Gene* 187:9-18). Non-mammalian cells can be modified to replicate human glycosylation (Li et al., 2006, *Nature Biotechnol.* 24:210-215). Glycoengineered *Pichia pastoris* is an example of such a modified non-mammalian cell (Li et al., supra).

Patient Population

A "patient" refers to a mammal capable of being infected with *S. aureus*. In one preferred embodiment, the patient is a human. In alternative embodiments, the patient is a non-human mammal such as a dog or a cow. A patient can be treated prophylactically or therapeutically. Prophylactic treatment provides sufficient protective immunity to reduce the likelihood or severity of a *S. aureus* infection. Therapeutic treatment can be performed to reduce the severity of a *S. aureus* infection.

Prophylactic treatment can be performed using a pharmaceutical composition containing a polypeptide, immunogen or antibody described herein. Pharmaceutical compositions can be administered to the general population or to those persons at an increased risk of *S. aureus* infection.

Those "in need of treatment" include those already with an infection, as well as those prone to have an infection or in which a reduction in the likelihood of infection is desired. Persons with an increased risk of *S. aureus* infection include health care workers; hospital patients; patients with weakened immunity; patients facing therapy leading to a weakened immunity (e.g., undergoing chemotherapy or radiation therapy for cancer or taking immunosuppressive drugs); patients undergoing surgery; patients receiving foreign body implants (such a catheter or a vascular device); patients under diagnostic procedures involving foreign bodies; patients on renal dialysis and persons in professions having an increased risk of burn or wound injury. As used herein, "weakened immunity" refers to an immune system that is less capable of battling infections because of an immune response that is not properly functioning or is not functioning at the level of a normal healthy adult. Examples of patients with weakened immunity are patients that are infants, young children, elderly, pregnant or a patient with a disease that affects the function of the immune system such as HIV or AIDS.

Foreign bodies used in diagnostic or therapeutic procedures include indwelling catheters or implanted polymer device. Examples of foreign body-associated *S. aureus* infections include septicemia/endocarditis (e.g., intravascular catheters, vascular prostheses, pacemaker leads, defibrillator systems, prosthetic heart valves, and left ventricular assist devices); peritonitis (e.g., ventriculo-peritoneal cerebrospinal fluid (CSF) shunts and continuous ambulatory peritoneal dialysis catheter systems); ventriculitis (e.g., internal and external CSF shunts); and chronic polymer-associated syndromes (e.g., prosthetic joint/hip loosening, fibrous capsular contracture syndrome after mammary argumentation with silicone prosthesis and late-onset endophtalmisis after implantation of artificial intraocular lenses following cataract surgery). (See, Hellmann and Peters, Biology and Pathogenicity of *Staphylococcus epidermidis*, In: Gram Positive Pathogens, Eds. Fischetti et al., American Society for Microbiology, Washington D.C. 2000.)

Non-human patients that can be infected with *S. aureus* include cows, pigs, sheep, goats, rabbits, horses, dogs, cats, rats and mice. Treatment of non-human patients is useful in both protecting pets and livestock (e.g. against Staph-related disease common to animals such as bovine mastitis) and evaluating the efficacy of a particular treatment. In addition to the obvious benefits of preventing, or reducing the likelihood or severity of clinical manifestations of *S. aureus* infections in vaccinated animals, additional benefits include the reduction of costs resulting from sick and underproductive livestock animals to a farmer; the reduction in the need for quarantine measures to a human or veterinary clinic by reducing the number of *S. aureus* infected patients, and reduced need for repeated rigorous decontamination of equipment and facilities; and a reduction of the number of *S. aureus* carriers in the human and animal populations, which reduces their potential contamination and spread to others.

In an embodiment, a patient is treated prophylactically in conjunction with a therapeutic or medical procedure involving a foreign body. In additional embodiments, the patient is immunized at about 2 weeks, 1 month, about 2 months or about 2-6 months prior to the procedure. In another embodiment, the patient is immunized prophylactically not in conjunction with a particular contemplated procedure. For vaccinations, boosters are delivered as needed. Additionally, patients treated prophylactically may also receive passive immunotherapy by administration of an antibody protective against *S. aureus* alone or in conjunction with vaccination.

Pharmaceutical Compositions

A further feature of the invention is the use of an SA2451 polypeptide, derivative or fragment thereof described herein ("immunogenic agent"), either alone or in combination with one or more additional antigens, in a composition, preferably an immunogenic composition or vaccine, for treating patients with an *S. aureus* infection, reducing the progression, onset or severity of pathological symptoms associated with *S. aureus* infection and/or reducing the likelihood of an *S. aureus* infection. Suitably, the composition comprises a pharmaceutically acceptable carrier.

In some embodiment of the invention described above, the pharmaceutical compositions are used in human patients. In alternative embodiments, the pharmaceutical compositions are used in non-human patients.

A "pharmaceutically-acceptable carrier" is meant to mean a liquid filler, diluent or encapsulating substance that may be safely used in systemic administration. Depending upon the particular route of administration, a variety of pharmaceutically acceptable carriers, well known in the art may be used. These carriers may be selected from a group including sugars, starches, cellulose and its derivatives, malt, gelatine, talc, calcium sulfate, vegetable oils, synthetic oils, polyols, alginic acid, phosphate buffered solutions including phosphate buffered saline, emulsifiers, isotonic saline, and pyrogen-free water. In particular, pharmaceutically acceptable carriers may contain different components such as a buffer, sterile water for injection, normal saline or phosphate-buffered saline, sucrose, histidine, salts and polysorbate. Terms such as "physiologically acceptable", "diluent" or "excipient" can be used interchangeably.

The above compositions may be used as therapeutic or prophylactic vaccines. Accordingly, the invention extends to the production of vaccines containing as active ingredients one or more of the immunogenic agents of the invention. Any suitable procedure is contemplated for producing such vaccines. Exemplary procedures include, for example, those described in New Generation Vaccines (1997, Levine et al., Marcel Dekker, Inc. New York, Basel Hong Kong), which is incorporated herein by reference.

A polypeptide of the invention can be fused or attached to an immunogenic carrier. Useful carriers are well known in the art and include for example: thyroglobulin; albumins such as human serum albumin; toxins, toxoids or any mutant crossreactive material (CRM) of the toxin from tetanus, diphtheria, pertussis, *Pseudomonas, E. coli, Staphylococcus*, and Streprococcus; polyamino acids such as poly(lysine: glutamic acid); influenza; Rotavirus VP6, Parvovirus VP1 and VP2; hepatitis B virus core protein; hepatitis B virus recombinant vaccine and the like. Alternatively, a fragment or epitope of a carrier protein or other immunogenic protein may be used. For example, a peptide of the invention can be coupled to a T cell epitope of a bacterial toxin, toxoid or CRM. In this regard, reference may be made to U.S. Pat. No. 5,785,973, which is incorporated herein by reference.

Administration/Methods of Treatment

An SA2451 polypeptide, derivative or fragment thereof (alone or in combination with one or more immunogens) or an antibody described herein can be formulated and administered to a patient using the guidance provided herein along with techniques well known in the art. Guidelines for pharmaceutical administration in general are provided in, for example, Vaccines Eds. Plotkin and Orenstein, W.B. Sanders Company, 1999; Remington's Pharmaceutical Sciences 20th Edition, Ed. Gennaro, Mack Publishing, 2000; and Modern Pharmaceutics 2nd Edition, Eds. Banker and Rhodes, Marcel Dekker, Inc., 1990.

Accordingly, the invention provides a method for inducing a protective immune response in a patient against an S. aureus infection comprising the step of administering to the patient an immunologically effective amount of any of the vaccines or pharmaceutical compositions described herein. In one embodiment of this aspect of the invention, the patient is a human. In alternative embodiments, the patient is a non-human mammal.

Also provided by the invention is a method for treating S. aureus infection, or for treating any pathological condition associated with S. aureus infection, the method comprising the step of administering to the patient an immunologically effective amount of any of the vaccines or pharmaceutical compositions described herein. In one embodiment of this aspect of the invention, the patient is a human. In alternative embodiments, the patient is a non-human mammal.

Vaccines and/or antibodies can be administered by different routes such as subcutaneous, intramuscular, intravenous, mucosal, parenteral or transdermal. Subcutaneous and intramuscular administration can be performed using, for example, needles or jet-injectors.

In some embodiments, the vaccines and/or antibodies of the invention can be formulated in or on virus-like particles (see, e.g., International Publication Nos. WO94/20137; WO96/11272; U.S. Pat. Nos. 5,985,610; 6,599,508; 6,361,778), liposomes (see, e.g., U.S. Pat. No. 5,709,879), bacterial or yeast ghosts (empty cells with intact envelopes; see, e.g., International Publication WO 92/01791, US Publication No. 2009/0239264 and 2008/0003239, U.S. Pat. No. 6,951,756), and outer membrane vesicles or blebs (de Moraes et al., 1992, Lancet 340: 1074 and Bjune et al., 1991, Lancet 338: 1093).

The compositions described herein may be administered in a manner compatible with the dosage formulation, and in such amount as is immunogenically-effective to treat and/or reduce the likelihood of S. aureus infection. The dose administered to a patient, in the context of the present invention, should be sufficient to effect a beneficial response in a patient over time such as a reduction in the level of S. aureus, or to reduce the likelihood of infection by S. aureus. The quantity of the immunogenic agent(s) to be administered may depend on the subject to be treated inclusive of the age, sex, weight and general health condition thereof. In this regard, precise amounts of the immunogenic agent(s) required to be administered will depend on the judgment of the practitioner. In determining the effective amount of the immunogenic agent to be administered in the treatment or prophylaxis against S. aureus, the physician may evaluate circulating plasma levels, progression of disease, and the production of anti-S. aureus antibodies. In any event, suitable dosages of the immunogenic agents of the invention may be readily determined by those of skill in the art. Such dosages may be in the order of nanograms to milligrams of the immunogenic agents of the invention.

Suitable dosing regimens are preferably determined taking into account factors well known in the art including age, weight, sex and medical condition of the patient; the route of administration; the desired effect; and the particular compound employed. The vaccine and/or antibody composition can be used in multi-dose formats. It is expected that a dose for a vaccine composition would consist of the range of 1.0 µg to 1.0 mg total polypeptide. In different embodiments of the present invention, the dosage range is from 5.0 µg to 500 µg, 0.01 mg to 1.0 mg, or 0.1 mg to 1.0 mg. When more than one polypeptide is to be administered (i.e., in combination vaccines), the amount of each polypeptide is within the described ranges.

It is expected that a dose for a passive immunity composition of the invention would consist of the range of 1 µg/kg to 100 mg/kg of antibody. In different embodiments, of the present invention, the dosage range is from 1 µg/kg to 15 mg/kg, 0.05 mg/kg to about 10 mg/kg, 0.5 mg/kg to 2.0 mg/kg, or 10 mg/kg to 50 mg/kg.

The timing of doses depends upon factors well known in the art. After the initial administration one or more additional doses may be administered to maintain and/or boost antibody titers.

For combination vaccinations, each of the polypeptides can be administered together in one composition or separately in different compositions. An SA2451 polypeptide described herein is administered concurrently with one or more desired immunogens. The term "concurrently" is not limited to the administration of the therapeutic agents at exactly the same time, but rather it is meant that the SA2451 polypeptides described herein and the other desired immunogen(s) are administered to a subject in a sequence and within a time interval such that the they can act together to provide an increased benefit than if they were administered otherwise. For example, each therapeutic agent may be administered at the same time or sequentially in any order at different points in time; however, if not administered at the same time, they should be administered sufficiently close in time so as to provide the desired therapeutic effect. Each therapeutic agent can be administered separately, in any appropriate form and by any suitable route.

All publications mentioned herein are incorporated by reference for the purpose of describing and disclosing methodologies and materials that might be used in connection with the present invention. Nothing herein is to be construed as an admission that the invention is not entitled to antedate such disclosure by virtue of prior invention.

Having described preferred embodiments of the invention with reference to the accompanying drawings, it is to be understood that the invention is not limited to those precise embodiments, and that various changes and modifications may be effected therein by one skilled in the art without departing from the scope or spirit of the invention as defined in the appended claims.

The following examples illustrate, but do not limit the invention.

Example 1

Cloning and Expression of Antigen

Genomic DNA was purified from S. aureus COL strain MB5393 and used as a template for PCR. The SA2451 gene (SEQ ID NO:3) was amplified by PCR in a 50 µL volume reaction prepared in duplicate. Each reaction mixture contained 250 ng genomic DNA, 125 ng each forward (CAC-CATGAAGAAAATTAAATATATACTTGTCGTGTTT-GTCTTATCGC; SEQ ID NO:4) and reverse (TCAGTGGTGGTGGTGGTGGTGGTGGTGCTTAT-GACCACCTTTCTGTTTA; SEQ ID NO:5) primer, 1 µL 10 mM dNTPs, 2.5 units of native Pfu polymerase and 1× Pfu buffer (Stratagene, La Jolla Calif.). The thermocycling conditions were as follows: one cycle of 94° C. for 5 minutes; 30 cycles of 94° C. for 45 seconds, 56° C. for 45 seconds, 72° C. for one minute; one cycle of 72° C. for 10 minutes. The amplified DNA sequence (966 bp) was digested with the appropriate restriction enzymes and gel-purified using GENE CLEAN II® (QBIOgene, Carlsbad, Calif.) according to the manufacturer's directions. The DNA was ligated into the pENTR/Sd/D vector using the NdeI/Bpu1102I sites that had been engineered into the PCR primers and introduced into E. coli NovaBlue competent cells (EMD Biosciences).

The SA2451 gene (SEQ ID NO:3) was cloned into an expression vector (pET-28b) that would facilitate either a carboxy or amino his tag to be added to the expressed protein. E. coli competent cells were transformed with the vector containing a nucleotide sequence encoding SA2451 ORF with a histidine tag and grown on LB plates containing ampicillin (100 µg/mL) and chloramphenicol (34 ng/ml). To test for expression of SA2451, an isolated colony was inoculated into 5 mL of liquid LB, 1% glucose, 100 µg/ml ampicillin, and incubated at 37° C. or 25° C., 250 rpm, until the $OD_{600}$ was between 0.5 to 1.0. A 1.0 ml culture volume of cells was subjected to centrifugation and resuspended in lysis buffer. The mixtures were held on ice for 5 minutes and subsequently sonicated three times for ten seconds, each with cooling in between. To obtain "soluble" and "insoluble" fractions the mixture was centrifuged at 13,000 rpm for fifteen minutes at 4° C. The supernatant was designated "soluble" and the pellet was resuspended in lysis buffer and designated "insoluble."

Expression of SA2451 (C-Histag with glycine cap) was analyzed by Coomassie staining of SDS-PAGE gels run under reducing and denaturing conditions. The gels were stained with Bio-Safe Coomassie, a Coomassie G250 stain (BIO-RAD) according to the manufacturer's protocol. Western blot was performed and the signal was detected by anti-His mAb (EMD Sciences). A 36 kDa protein was specifically detected by both Coomasie staining and Western blot in lysates.

Direct scale-up of the above small scale procedure into stirred tank fermenters (30 liter scale) with a 20 liter working volume was achieved. Inoculum was cultivated in a 250 mL flask containing 50 mL of LB medium (plus ampicillin) and inoculated with 1 mL of frozen seed culture and cultivated for 6 hours. One mL of this seed was used to inoculate a 2 liter flask containing 500 mL of LB medium (plus ampicillin) and incubated for 16 hours. A large scale fermenter (30 liter scale) was cultivated with 20 liters of LB medium (plus ampicillin). The fermentation parameters of the fermenter were: pressure=5 psig, agitation speed=300 rpm, airflow=7.5 liters/minute and temperature=25° C. Cells were incubated to an optical density (OD) of 1.3 optical density units at a wavelength of 600 nm. Cells were harvested by lowering the temperature to 15° C., concentrated by passage through a 500KMWCO hollow fiber cartridge, and centrifuged at 8,000 times gravity at 4° C. for 20 minutes. Supernatants were decanted and the recombinant E. coli wet cell pellets were frozen at −70° C.

Frozen recombinant E. coli cell paste (56 grams) was thawed and resuspended in 565 mL of IMAC Buffer A (50 mM NaCl, 5 mM Imidazole, 20 mM Tris, 125 mM Brij-35, 10 mM TritonX-100, 5 mM Tween 20, pH 7.5; BSB-protease inhibitor cocktail). A lysate was prepared with a PANDA cell homogenizer (Niro Soavi). The lysate was clarified by centrifugation at 30,000×g for 60 minutes at 4° C. using a Beckman JA-21 centrifuge with a JA-18 rotor. The supernatant was added to a 10 ml column gravity packed with Ni Sepharose 6 Fast Flow resin (GE Healthcare) connected to an AKTA FPLC previously equilibrated with 10 CV of IMAC Buffer A. Following a 10CV wash of the column with 2% IMAC Buffer B (IMAC Buffer A+1 M Imidazole), bound protein was eluted in 5 ml fractions at 5 ml/min using a linear imidazole gradient of 2-100% IMAC Buffer B. Fractions containing protein were analyzed by SDS-PAGE followed by coomassie staining and Western Blotting using anti-His antibody. The fractions were pooled based on SDS-PAGE data and the pooled volume was dialyzed against S Buffer A (20 mM MES, pH 6.5, 20 mM KCl) overnight at 4° C. A HiTrap SPFF column (2×5 ml cartridges, GE Healthcare) was connected to an ÄKTA FPLC and was equilibrated with 10 CV of S Buffer A after being charged with S Buffer B (20 mM MES, pH 6.5, 1 M KCl). The pool was loaded onto the column (GE Healthcare) at a flow rate of 5 ml/min, and the column was washed with S Buffer A at a flow rate of 5 ml/min. Following a 2% S Buffer B wash, bound protein was eluted in 5 ml size fractions at 5 ml/min using a linear KCl gradient of 2-100% S Buffer B. Protein containing fractions were analyzed by SDS-PAGE followed by Coomassie-staining or Western blotting (anti-His antibody). SA2451 containing fractions were pooled and dialyzed against a final buffer (10 mM MOPS, 150 mM NaCl, pH 7.0) overnight at 4° C. The protein solution was concentrated to 0.2 mg/mL and processed to remove endotoxin and frozen at −70° C. The protein was thawed and adsorbed onto aluminum hydroxyphosphate adjuvant ("Merck Aluminum Adjuvant" or "MAA") at a final concentration of 0.1 mg/mL. This protein was used in immunogenicity and protection studies.

Example 2

Immunogenicity Studies

Balb/c mice, at 3-5 weeks of age, were immunized on days 0, 7 and 21 intramuscularly with a formulation of His-tagged SA2451 (20 µg per injection) adsorbed onto MAA. Negative control mice were injected with bovine serum albumin (BSA) formulated on MAA, or not immunized. Immune sera from the mice was tested for reactivity to SA2451 by ELISA and was found to contain high antibody titers to the antigen. Negative control antisera did not have antibody titers to SA2451 (Data not shown). Immune sera was also analyzed for reactivity to S. aureus cells by Flow cytometry. Results show the antigen was immunogenic in Balb/c mice.

Example 3

Murine Lethal Challenge Model

Figure 4B:
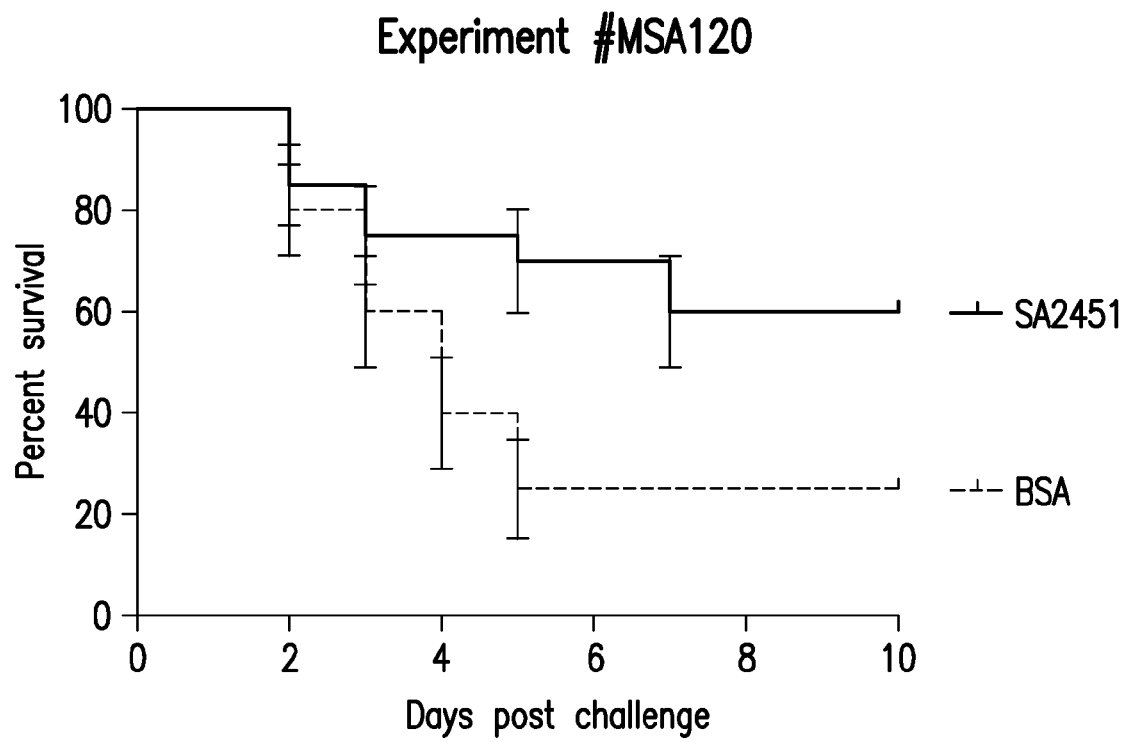
Figure 5:
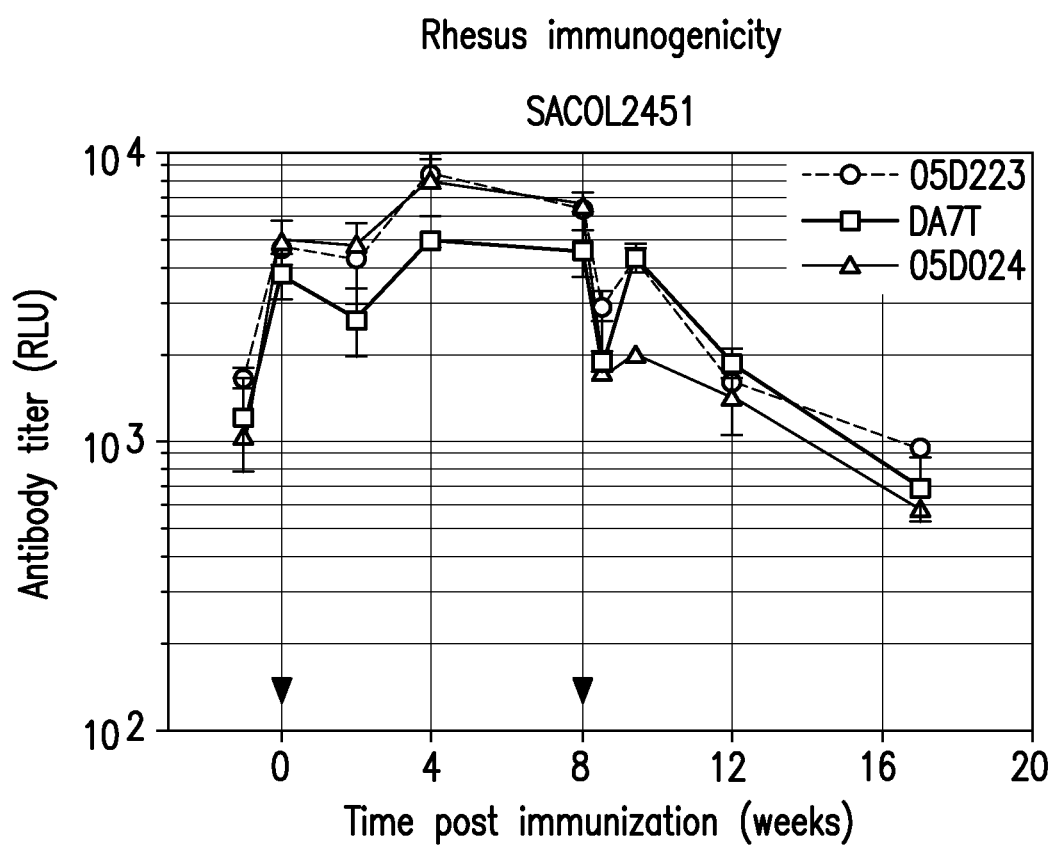
FIG. 5 shows the results of an immunogenicity study in which rhesus macaques were immunized intramuscularly with SA2451 formulated on MAA. The animals were challenged via the IV route with a sublethal dose of S. aureus Becker. The antibody response to the antigen was measured using an ELISA technique with a Mesoscale instrument (see Example 4).

In two independent experiments, Balb/c mice immunized with either SA2451 or BSA formulated on MAA (20 per group) or unimmunized (see EXAMPLE 2) were challenged with S. aureus Becker ($8 \times 10^8$ CFU/mouse) injected via the tail vein two weeks after immunization. Mice were monitored for survival for a period of 10 days post challenge. At the end of the first experiment (#MSE116), 8 mice survived in the SA2451 polypeptide-immunized group, compared to 2 surviving in the BSA control group. Thus, the group of mice immunized with SA2451 had a significantly enhanced survival rate compared to the negative control mice immunized with BSA (p=0.0027). In the second experiment (#MSE120), 12 mice survived in the SA2451 polypeptide-immunized group, compared to 5 surviving in the BSA control group. Results are shown for the two experiments in FIG. 3 and survival curves are compared in FIG. 4. Similar to the first experiment, mice immunized with SA2451 had a significantly enhanced survival rate compared to the negative control mice immunized with BSA (p=0.0250).

Example 4

Rhesus Macaque Immunogenicity

Rhesus macaques (n=3) were immunized with 50 µg of SA2451 formulated on Merck alum adjuvant (MAA), intramuscularly, on day 0. Animals were bled at designated time points and the immune response to the antigen measured using an ELISA type assay, with a Mesoscale instrument (as per the manufacturer's instructions). The titers are measured in RLU (relative luminescence units). The monkeys' titers were increased by 4 weeks post immunization. At eight weeks post immunization, the animals were challenged via the intravenous route with a sublethal dose of *S. aureus* Becker ($2 \times 10^{9}$ CFU). Measurement of immune titers post challenge indicated that two of three monkeys had increased Ab titers to the bacteria, indicating a memory response to the antigen on the bacteria.

What is claimed is:

1. A method of inducing an immune response in a patient against *Staphylococcus aureus* infection comprising administering an immunologically effective amount of the polypeptide of SEQ ID NO: 1, a pharmaceutically acceptable carrier and an adjuvant.

2. The method of claim 1 wherein the patient is human or a non-human mammal.

3. The method of claim 2 wherein the patient has weakened immunity, has received a foreign body implant or is on renal dialysis.

4. The method of claim 3 wherein the patient that has weakened immunity has a Human Immunodeficiency Virus (HIV) infection or Acquired Immune Deficiency Syndrome (AIDS).

5. The method of claim 3 wherein the foreign body implant is a catheter, a vascular device, pacemaker leads, defibrillator systems, or prosthetic heart valve.

6. The method of claim 1, wherein the composition further comprises one or more additional *S. aureus* antigens.

* * * * *